(12) United States Patent
Schwartz et al.

(10) Patent No.: US 11,940,510 B2
(45) Date of Patent: Mar. 26, 2024

(54) SYSTEMS AND METHOD FOR GENERATION OF HYPERPOLARIZED MATERIALS

(71) Applicants: NVISION IMAGING TECHNOLOGIES GMBH, Ulm (DE); UNIVERSITÄT ULM, Ulm (DE)

(72) Inventors: Ilai Schwartz, New-Ulm (DE); Michael Keim, Neu-Ulm (DE); Martin Plenio, Ulm (DE); Benedikt Tratzmiller, Ulm (DE)

(73) Assignees: NVision Imaging Technologies Gmbh, Ulm (DE); Universität Ulm, Ulm (DE)

( * ) Notice: Subject to any disclaimer, the term of this patent is extended or adjusted under 35 U.S.C. 154(b) by 0 days.

(21) Appl. No.: 17/995,232

(22) PCT Filed: Mar. 31, 2021

(86) PCT No.: PCT/IB2021/000202
§ 371 (c)(1),
(2) Date: Sep. 30, 2022

(87) PCT Pub. No.: WO2021/198776
PCT Pub. Date: Oct. 7, 2021

(65) Prior Publication Data
US 2023/0152399 A1 May 18, 2023

Related U.S. Application Data

(60) Provisional application No. 63/055,367, filed on Jul. 23, 2020, provisional application No. 63/052,102, (Continued)

(51) Int. Cl.
*G01R 33/28* (2006.01)
*A61K 49/10* (2006.01)
(Continued)

(52) U.S. Cl.
CPC ............ *G01R 33/282* (2013.01); *A61K 49/10* (2013.01); *C07C 67/14* (2013.01); *C07C 67/293* (2013.01);
(Continued)

(58) Field of Classification Search
CPC .................. G01R 33/282; G01R 33/4608; G01R 33/445; A61K 49/10; C07C 67/14;
(Continued)

(56) References Cited

U.S. PATENT DOCUMENTS

| | | | |
|---|---|---|---|
| 6,278,893 B1 * | 8/2001 | Ardenkjær-Larson et al. | A61K 49/10 324/309 |
| 2004/0024307 A1 * | 2/2004 | Golman | G01R 33/62 600/420 |

OTHER PUBLICATIONS

Barskiy et al., "Rapid Catalyst Capture Enables Metal-Free para-Hydrogen-Based Hyperpolarized Contrast Agents", The Journal of Physical Chemistry Letters 2018 9 (11), 2721-2724.
(Continued)

*Primary Examiner* — G. M. A Hyder
(74) *Attorney, Agent, or Firm* — Finnegan, Henderson, Farabow, Garrett & Dunner, LLP

(57) ABSTRACT

A method for preparing an NMR material, comprising generating parahydrogen in gas or liquid form at a first location; transporting the parahydrogen away from the first location; mixing a precursor compound including a metabolite component with a catalyst for hydrogenation; hydrogenating the precursor compound using the parahydrogen; transferring polarization in the precursor compound to a nuclear spin of the metabolite component; cleaving a side arm of the precursor compound in a chemical reaction, with the metabolite molecule being one of the products of the reaction; separating the metabolite molecule from the catalyst for hydrogenation and other products of the reaction;
(Continued)

and generating metabolite molecules for use in an MRI scanner by extracting a sample of the metabolite molecule having at least 5% polarization.

25 Claims, 11 Drawing Sheets

Related U.S. Application Data filed on Jul. 15, 2020, provisional application No. 63/002,395, filed on Mar. 31, 2020.

(51) Int. Cl.
| | |
|---|---|
| *C07C 67/14* | (2006.01) |
| *C07C 67/293* | (2006.01) |
| *C07C 69/716* | (2006.01) |
| *C07F 7/08* | (2006.01) |
| *G01R 33/46* | (2006.01) |
| *G01R 33/44* | (2006.01) |

(52) U.S. Cl.
CPC ............ *C07C 69/716* (2013.01); *C07F 7/081* (2013.01); *C07F 7/083* (2013.01); *G01R 33/4608* (2013.01); *C07B 2200/05* (2013.01); *G01R 33/445* (2013.01)

(58) Field of Classification Search
CPC ..... C07C 67/293; C07C 69/716; C07F 7/081; C07F 7/083; C07B 2200/05
See application file for complete search history.

(56) References Cited

OTHER PUBLICATIONS

Kidd et al. "Facile Removal of Homogeneous SABRE Catalysts for Purifying Hyperpolarized Metronidazole, a Potential Hypoxia Sensor", The Journal of Physical Chemistry C 2018 122 (29), 16848-16852.
Bär, S. et al., (2012), "On the spin order transfer from parahydrogen to another nucleus", Journal of Magnetic Resonance., vol. 225, pp. 25-35.
Coffey, A. M. et al., (2016), "Open-Source Automated Parahydrogen Hyperpolarizer for Molecular Imaging Using 13 C Metabolic Contrast Agents", Analytical Chemistry, vol. 88, No. 16, pp. 8279-8288.
Coffey, A. M. et al., (2016), "S-1 Supporting Information for an Open-Source Automated Parahydrogen Hyperpolarizer for Molecular Imaging Using 13 C Metabolic Contrast Agents", pp. 1-26. Retrieved from the internet on Jul. 22, 2021 URL:https://pubs.acs.org/doi/suppl/10.1021/acs.analchem.6b02130/suppl-file/ac6b02130si001.pdf.
Korchak, S. et al., (2018), "Pulsed Magnetic Resonance to Signal-Enhance Metabolites within Seconds by utilizing para-Hydrogen", Chemistry Open, vol. 7, No. 5, pp. 344-348.
Reineri, F. et al., (2015), "ParaHydrogen Induced Polarization of 13C carboxylate resonance in acetate and pyruvate", Nature Communications, 6:5858 (6 pgs.).
Souza, A. M. et al., (2011), "Robust dynamical decoupling for quantum computing and quantum memory", arxiv.org, vol. 106, No. 24, Cornell University Library, Ithaca, NY.
International Search Report and Written Opinion of the International Searching Authority received in relation to International Application No. PCT/IB2021/000202, dated Oct. 4, 2021, (20 pages.).

\* cited by examiner

200

```
┌─────────────────────────────────────┐
│ Parahydrogenate Precursor Molecules │
│                 201                 │
└─────────────────────────────────────┘
                  │
                  ▼
┌─────────────────────────────────────┐
│   Transfer Spin Order to Sidearm    │
│                 203                 │
└─────────────────────────────────────┘
                  │
                  ▼
┌─────────────────────────────────────┐
│  Transfer Polarization to 13C Spin  │
│       in the Target Molecule        │
│                 205                 │
└─────────────────────────────────────┘
                  │
                  ▼
┌─────────────────────────────────────┐
│ Separate Polarized Target Molecules │
│       from Polarized Precursors     │
│                 207                 │
└─────────────────────────────────────┘
```

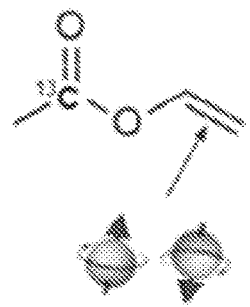

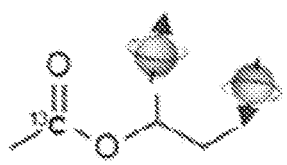

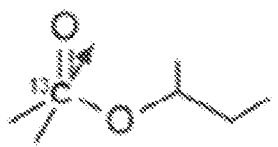

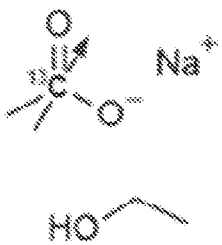

FIG. 2

SYSTEMS AND METHOD FOR GENERATION OF HYPERPOLARIZED MATERIALS

CROSS-REFERENCES TO RELATED APPLICATIONS

This application is a U.S. national stage entry under 35 U.S.C. § 371 of international application no. PCT/IB2021/000202, filed Mar. 31, 2021, which designates the U.S. and claims priority to U.S. Provisional Patent Application No. 63/002,395, filed Mar. 31, 2020, U.S. Provisional Patent Application No. 63/002,395, filed Mar. 31, 2020, U.S. Provisional Patent Application No. 63/052,102, filed Jul. 15, 2020 and U.S. Provisional Patent Application No. 63/055, 367, filed Jul. 23, 2020. The contents of these applications are herein incorporated by reference in their entirety

TECHNICAL FIELD

The disclosed embodiments generally relate to generation of hyperpolarized materials for use in nuclear magnetic resonance, magnetic resonance imaging, or similar applications.

BACKGROUND

Parahydrogen induced polarization (PHIP) is a method for polarizing metabolites for hyperpolarized (HP) Magnetic Resonance Imaging (MRI), with low cost and high throughput. Parahydrogen induced polarization with side arm hydrogenation (PHIP-SAH) can be used to polarize metabolites, e.g. acetate molecules. Existing PHIP-SAH polarization approaches may be unsuitable for preclinical or clinical HP MRI applications. Due to various effects, such as radiation damping, such approaches may be unable to achieve a sufficient volume or concentration of sufficiently polarized samples.

SUMMARY

The disclosed embodiments include a system for increasing nuclear spin polarization. The system can include a chamber. The chamber can be configurable to contain at least 1 milliliter (mL) of a solution including a precursor at a concentration of between 10 and 1000 millimolar (mM). The system can include a radiofrequency (RF) coil disposed around the chamber, the RF coil including a proton ($^1$H) channel and a carbon-13 ($^{13}$C) channel. The system can include a magnetic field source configured to generate a magnetic field. The magnetic field can have, within the chamber, a mean magnetic field strength between 1 and 5000 millitesla (mT) and a magnetic field inhomogeneity between 1 and 250 microtesla (μT). The system can include a flow manifold coupled to a gas-liquid exchange mechanism configurable to mix parahydrogen gas with the solution to generate a parahydrogenated precursor. The system can include a waveform generator configurable to generate a polarized precursor by providing RF stimulation to the RF coil, a nuclear spin polarization of the polarized precursor at least 5%. The RF stimulation can include: (i) a first pulse sequence, provided to the $^1$H channel, comprising at least one $^1$H excitation pulse and a first set of at least ten $^1$H dynamic decoupling pulses; and (ii) a second pulse sequence, provided to the $^{13}$C channel, comprising at least one $^{13}$C excitation pulse, and a second set of at least ten $^{13}$C dynamic decoupling pulses.

The disclosed embodiments include a method for increasing a nuclear spin polarization. The method can include generating a parahydrogenated precursor by flowing a parahydrogen gas into a chamber containing at least 1 milliliter (mL) of a solution. The solution can include a precursor at a concentration of between 10 and 1000 millimolar (mM). The chamber can be disposed within a magnetic field. The magnetic field can have a mean magnetic field strength of between 1 and 5000 millitesla (mT) and a magnetic field inhomogeneity of between 1 and 250 microtesla (μT) within the chamber. The method can include mixing the parahydrogen gas with the solution. The method can include generating a polarized precursor by applying a first pulse sequence and a second pulse sequence to increase the nuclear spin polarization of the parahydrogenated precursor to at least 5%. The first pulse sequence can include at least one proton ($^1$H) excitation pulse and a first set of a least ten $^1$H dynamic decoupling pulses. The second pulse sequence can include at least one carbon-13 ($^{13}$C) excitation pulse and a first set of a least ten $^{13}$C dynamic decoupling pulses.

The disclosed embodiments include a method for preparing a polarized target molecule that can be used in a magnetic resonance operation. The method can include generating and storing parahydrogen at a first location and transporting the parahydrogen from the first location to a second location different from the first location and at the second location. The method can include generating a solution of a parahydrogenated precursor by mixing the parahydrogen with a solution of a precursor in the presence of a hydrogenation catalyst. The method can include generating, using the solution of the parahydrogenated precursor, a solution of a polarized precursor by transferring polarization from protons associated with the parahydrogen in the parahydrogenated precursor to at least one nuclear spin of the parahydrogenated precursor. In this manner a polarization in the solution of the polarized precursor of at least 5% in the at least one nuclear spin may be obtained. The method can include generating, using the solution of the polarized precursor, a solution of a polarized target molecule by cleaving the polarized target molecule from the polarized precursor. The method can include generating, using the solution of a polarized target molecule, a second solution of the polarized target molecule by separating the hydrogenation catalyst from the second solution of the polarized target molecule. The second solution of the polarized target molecule can have a concentration of at least 100 mM of the target molecule.

The disclosed embodiments include a compound of Formula I,

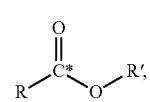

tautomers, deuterated derivatives and their tautomers, or pharmaceutically acceptable salts, thereof, and $^{13}$C enriched derivatives of any of the foregoing, wherein C* denotes $^{13}$C which denotes a carbon atom at the ester carbonyl center that is naturally $^{13}$C enriched or, optionally, a $^{13}$C labeled carboxylate carbon atom which can optionally undergo $^{13}$C hyperpolarization; R is a linear, branched, or cyclic $C_1$-$C_{10}$ alkyl group, in which one or more C atoms may be replaced by CO, COOH, $CH_2COOH$, $CONH_2$, and R is optionally substituted with, one or more group(s) selected from a CO, an OH, an amino (NR$^1$R$^2$), a halogen atom(s), a halo-alkyl group(s), or a carbocycle, wherein the carbocycle is optionally substituted with an aliphatic or aromatic ring, which is optionally substituted by one or more functional groups and R' is a linear, branched or cyclic hydrocarbon C$_1$-C$_{10}$ alkyl group containing an unsaturated bond in a two-bond distance from C*, in which one or more C atoms maybe be replaced by CO, COOH, CH$_2$COOH, CONH$_2$, and R' is optionally substituted with, one or more functional group(s), selected from a halogen, a halo-alkyl group, a carbocycle, wherein the carbocycle is optionally substituted with an aliphatic or aromatic ring, which is optionally substituted by one or more functional groups; R$^1$ and R$^2$ are each independently selected from H, $^2$H, $^3$H and an amino protecting group, optionally selected from trifluoroacetyl, acetyl, benzoyl, carbobenzoxy, tert-butyl carbonate and benzyl.

The disclosed embodiments include a compound of Formula II,

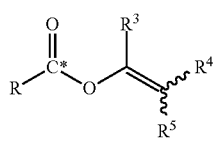

(II)

wherein, R is a linear, branched, or cyclic C$_1$-C$_{10}$ alkyl group, in which one or more C atoms maybe be replaced by CO, COOH, CH$_2$COOH, CONH$_2$, and R is optionally substituted with, one or more group(s) selected from carbonyl (C=O), hydroxyl (—OH), amino (NR$^1$R$^2$), halogen atom(s), halo-alkyl group(s), or by a carbocycle optionally substituted with an aliphatic or aromatic ring, which is, in its turn, optionally substituted by one or more functional groups; R$^1$ and R$^2$ are each independently selected from H, $^2$H, $^3$H and an amino protecting group, optionally selected from trifluoroacetyl, acetyl, benzoyl, carbobenzoxy, tert-butyl carbonate and benzyl; R$^3$, R$^4$, and R$^5$ are each independently H or a linear, branched, or cyclic C$_1$-C$_{10}$ alkyl hydrocarbon, wherein no more than two of the three of R$^3$, R$^4$, and R$^5$ may be a proton or deuterated species, thereof, the hydrocarbon is optionally substituted with one or more group(s) selected from a C$_6$ aryl, benzyl, phenyl, heteroaryl, halogen, a haloalkyl, an optionally substituted carbocycle, and an optionally substituted heterocycle, which is, each in its turn, optionally substituted by one or more functional groups selected from alkyl, alkoxy, or a heteroatom, such as N, O, Si, P, S, or a halogen, such as F, Cl, Br, I, that may also be further substituted.

The disclosed embodiments include a compound of Formula IIa

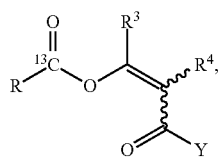

(IIa)

wherein R is a linear, branched, or cyclic C$_1$-C$_{10}$ alkyl group, in which one or more C atoms maybe be replaced by CO, COOH, CH$_2$COOH, CONH$_2$, and R may be optionally substituted with, one or more group(s) selected from carbonyl (C=O), hydroxyl (—OH), amino (NR$^1$R$^2$), halogen atom(s), halo-alkyl group(s), or by a carbocycle optionally substituted with an aliphatic or aromatic ring, which is, in its turn, optionally substituted by one or more functional groups; R$^1$ and R$^2$ are each independently selected from H, $^2$H, $^3$H and an amino protecting group, optionally selected from trifluoroacetyl, acetyl, benzoyl, carbobenzoxy, tert-butyl carbonate and benzyl; R$^3$ and R$^4$ are each independently H or a linear, branched, or cyclic C$_1$-C$_{10}$ alkyl hydrocarbon, wherein the hydrocarbon is optionally substituted with one or more group(s) selected from a C$_6$ aryl, benzyl, phenyl, heteroaryl, halogen, a haloalkyl, an optionally substituted carbocycle, and an optionally substituted heterocycle, which is, each in its turn, optionally substituted by one or more functional groups selected from alkyl, alkoxy, or a heteroatom, such as N, O, Si, P, S, or a halogen, such as F, Cl, Br, I, that may also be further substituted; Y is selected from R$^x$, OR$^x$, SR$^x$, NR$^x_2$, or H, wherein R$^x$ is alkyl (C$_1$-C$_{10}$), cycloalkyl (C$_3$-C$_{10}$), aryl (C$_6$-C$_{10}$), heteroaryl, or H wherein one or more C atoms may be optionally substituted with alkyl (C$_1$-C$_6$), or aryl (C$_6$-C$_{10}$).

The disclosed embodiments include a compound of formula IIb,

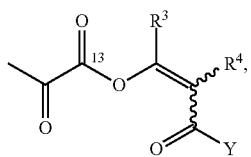

(IIb)

wherein R$^3$ and R$^4$ are each are each independently H or a linear, branched, or cyclic C$_1$-C$_{10}$ alkyl hydrocarbon, wherein the hydrocarbon is optionally substituted with one or more group(s) selected from a C$_6$ aryl, benzyl, phenyl, heteroaryl, halogen, a haloalkyl, an optionally substituted carbocycle, and an optionally substituted heterocycle, which is, each in its turn, optionally substituted by one or more functional groups selected from alkyl, alkoxy, or a heteroatom, such as N, O, Si, P, S, or a halogen, such as F, Cl, Br, I that may also be further substituted; Y is R$^x$, OR$^x$, SR$^x$, NR$^x_2$, or H, wherein R$^x$ is selected from alkyl (C$_1$-C$_{10}$), aryl (C$_6$-C$_{10}$), heteroaryl, or H wherein one or more C atoms may be optionally substituted with alkyl (C$_1$-C$_6$), or aryl (C$_6$-C$_{10}$).

The disclosed embodiments include a compound of formula IIc,

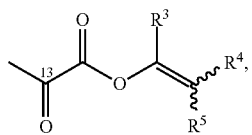

(IIc)

wherein R$_3$, R$_4$, and R$_5$ are each independently H or a linear, branched, or cyclic C$_1$-C$_{10}$ alkyl hydrocarbon, wherein no more than two of the three of R$^3$, R$^4$, and R$^5$ may be a proton or deuterated species, thereof, wherein the hydrocarbon is optionally substituted with one or more group(s) selected from a C$_6$ aryl, benzyl, phenyl, heteroaryl, halogen, a haloalkyl, an optionally substituted carbocycle, and an optionally substituted heterocycle, which is, each in its turn, optionally substituted by one or more functional groups selected from alkyl, alkoxy, or a heteroatom, such as N, O, Si, P, S, or a halogen, such as, F, Cl, Br, or I that may also be further substituted.

The disclosed embodiments include a compound according to Formula (III),

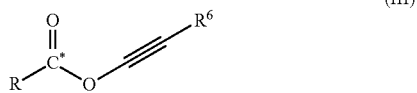

(III)

wherein, R is a linear, branched, or cyclic $C_1$-$C_{10}$ alkyl group, in which one or more C atoms maybe be replaced by CO, COOH, $CH_2COOH$, $CONH_2$, and R may be optionally substituted with, one or more group(s) selected from carbonyl (C=O), hydroxyl (—OH), amino ($NR^1R^2$), halogen atom(s), halo-alkyl group(s), or by a carbocycle optionally substituted with an aliphatic or aromatic ring, which is, in its turn, optionally substituted by one or more functional groups; $R^1$ and $R^2$ are each independently selected from H, $^2H$, $^3H$ and an amino protecting group, optionally selected from trifluoroacetyl, acetyl, benzoyl, carbobenzoxy, tert-butyl carbonate and benzyl; $R^6$ is H, or a linear, branched, or cyclic $C_1$-$C_{10}$ alkyl hydrocarbon, wherein the hydrocarbon is optionally substituted with one or more group(s) selected from a $C_6$-$C_{10}$ aryl, benzyl, phenyl, heteroaryl, halogen, a haloalkyl, an optionally substituted carbocycle, and an optionally substituted heterocycle aryl or cycloalkyl groups, which is, each in its turn, optionally substituted by one or more functional groups selected from alkyl, alkoxy, or a heteroatom, such as N, O, Si, P, S, or a halogen, such as F, Cl, Br, I that may also be further substituted.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which comprise a part of this specification, illustrate several embodiments and, together with the description, serve to explain the principles and features of the disclosed embodiments. In the drawings:

FIG. 2 illustrates an exemplary PHIP-SAH process, in accordance with disclosed embodiments.

FIG. 8 illustrates efficiency of ESOTHERIC with state of the art (CPMG-ref), Nested KDD and KDD4 refocusing pulses in a 0.5T magnetic field, 2.5 Gauss B1 field, with 200 ppm inhomogeneity and parabolic field profile, consistent with the disclosed embodiments.

DETAILED DESCRIPTION

Figure 1:
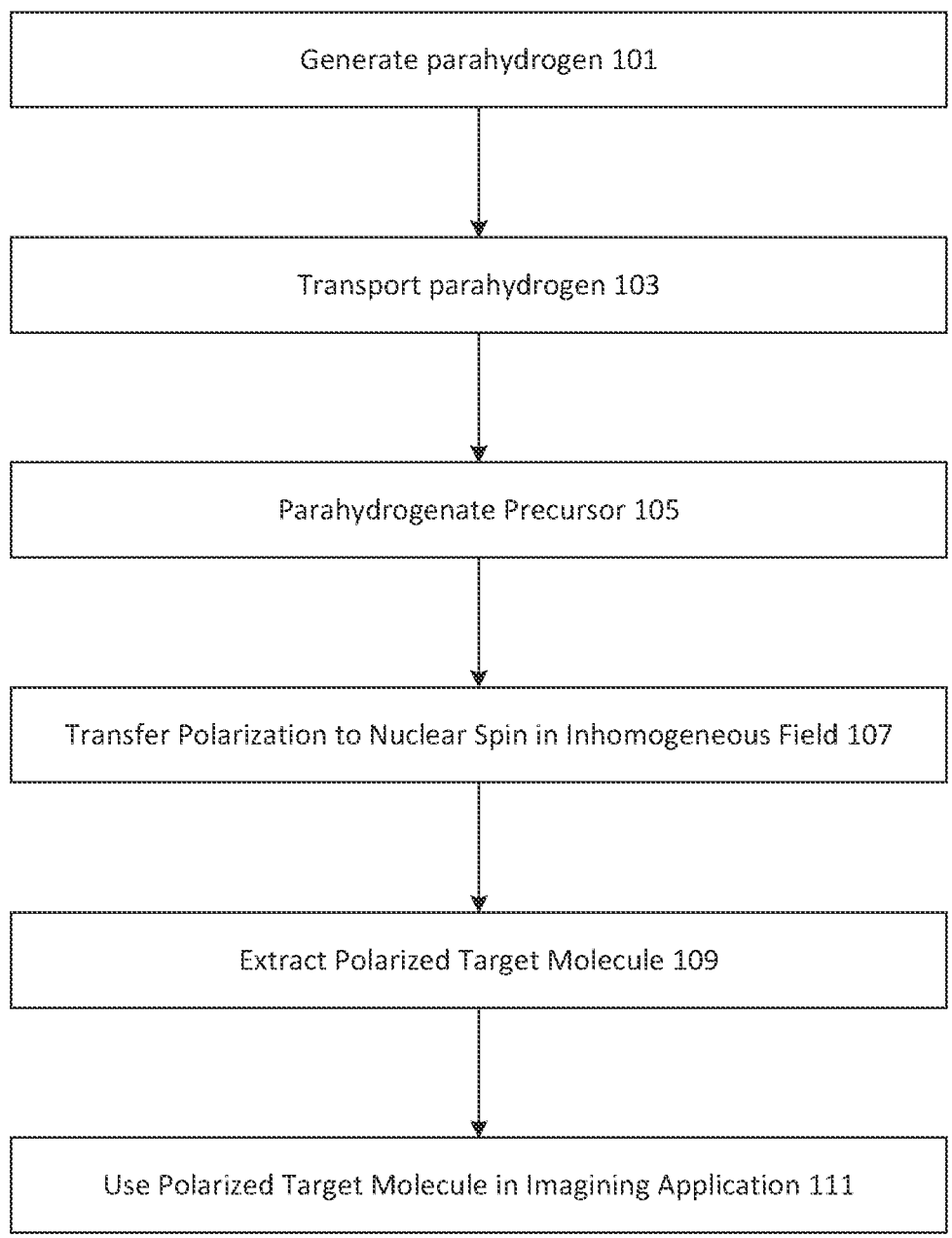
FIG. 1 depicts an exemplary process for generating polarized target materials for use in MRI/NMR application, in accordance with disclosed embodiments.

Reference will now be made in detail to exemplary embodiments, discussed with regards to the accompanying drawings. In some instances, the same reference numbers will be used throughout the drawings and the following description to refer to the same or like parts. Unless otherwise defined, technical and/or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Some preclinical or clinical hyperpolarized (HP) MRI applications require volumes of concentrated, polarized samples that can be difficult to produce using conventional polarization approaches. In some instances, the required concentration of polarized metabolites may exceed 200 mM. Existing polarization approaches may not achieve suitable polarization levels at such high concentrations. Such approaches may also be unable to scale production of samples to suitable volumes. Technical challenges involved in creating polarized volumes in excess of 10 ml can include challenges in creating a magnetic field in the range 100 mT-5000 mT with less than 100 ppm or 10 ppm inhomogeneity. Exciting large samples with RF pulses may also lead to smaller B1 fields (given specific power/amplification) and larger B1 inhomogeneities.

Envisioned embodiments include methods for preparing an NMR material. In some embodiments, an NMR material may be material suitable for use in NMR or MRI operations. In some embodiments, the NMR material may increase NMR/MRI signal and signal-to-noise ratio (SNR). In some embodiments, the NMR material can be suitable for use in solution NMR spectroscopy. In some embodiments, NMR material may be a chemical compound. In some embodiments, the NMR material may be a metabolite (e.g., a molecule with a biological relevance such as an amino acid, a saccharide, a derivative thereof, or the like), such as a metabolite suitable for use in an NMR metabolomics application. In some embodiments, the NMR material may be suitable for in-vitro probing of the metabolism of a cell culture or other biological tissue. In some embodiments, the NMR material may be used in an NMR probe to investigate a transient effect in which high signal enhancement due to hyperpolarization is needed, such proton exchange between water and biomolecules. In some embodiments, the NMR material can be a small molecule or metabolite suitable for injection into a cell, tissue or organism for detection in an MRI scan. In some embodiments, the NMR material can be introduced into a chamber for further analysis by NMR or MRI operations. In some embodiments, the NMR material can be enriched with $^{13}C$ atom(s).

Consistent with disclosed embodiments, NMR material can include target molecules. In some embodiments, the target molecules can be suitable for use in NMR or MRI operations. In some embodiments, the target molecule may increase NMR/MRI signal and signal-to-noise ratio (SNR). In some embodiments, the target molecule can be suitable for use in solution NMR spectroscopy. In some embodiments, the target molecule may be a metabolite (e.g., a molecule with a biological relevance such as an amino acid, a saccharide, a derivative thereof, or the like), such as a metabolite suitable for use in an NMR metabolomics application. In some embodiments, the target molecule may be suitable for in-vitro probing of the metabolism of a cell culture or other biological tissue. In some embodiments, the target molecule may be used in an NMR probe to investigate a transient effect in which high signal enhancement due to hyperpolarization is needed, such as proton exchange between water and biomolecules. In some embodiments, the target molecule can be a small molecule or metabolite suitable for injection into a cell, tissue or organism for detection in an MRI scan. In some embodiments, the target molecule can be introduced into a chamber for further analysis by NMR or MRI operations. In some embodiments, the target molecule can be enriched with $^{13}C$ atom(s).

Consistent with disclosed embodiments, the target molecule can be pyruvate, lactic acid, ketoglutaric acid, dehydroascorbic acid, natural and unnatural amino acids, esters thereof, and $^{13}C$ enriched versions, thereof.

Consistent with disclosed embodiments, a "precursor" can be a compound that includes the target molecule bound to a sidearm. In some embodiments, the precursor can be an ester molecule, with a generic formula of —COOR. Accordingly, the term "sidearm" may refer to the R moiety of the ester molecule. In preferred embodiments, the sidearm may include the substituents and functional groups directly bound to the ester oxygen bound by carbons on both sides. In some embodiments, the precursor can have one or multiple degrees of unsaturation that may undergo parahydrogenation and subsequent hyperpolarization. In some embodiments, the precursor can be an enol or ynol ester of the target molecule, wherein the specific enol or ynol may be referred to as the sidearm. As a non-limiting example, the target molecule can be pyruvate. When the precursor is vinyl pyruvate and the side arm is a vinyl functional group. When the precursor is cinnamyl pyruvate, the side arm is a phenyl allyl functional group. When the precursor is allyl pyruvate, the side arm is an allyl functional group. When the precursor is propargyl pyruvate, the side arm is a propargyl functional group.

Consistent with disclosed embodiments, a precursor can be reacted with parahydrogen (a form of molecular hydrogen) to form a parahydrogenated precursor. In some embodiments, the parahydrogen introduces additional covalently-bound hydrogen atoms onto the sidearm. In some embodiments, parahydrogen introduced to a precursor reacts at an unsaturated carbon-carbon bond. In some embodiments, parahydrogen introduced to a precursor reacts at an unsaturated carbon-carbon bond on the side arm.

Consistent with disclosed embodiments, a polarized precursor including a polarized target molecule can be generated by applying RF pulses to a parahydrogenated precursor to transfer the spin order to a net magnetization on a nuclear spin of choice of the target molecule. The polarized target molecule can then be cleaved from the sidearm. In some embodiments, the polarized target molecule can then be used for an NMR or MRI application.

Preparing NMR Material

As illustrated in FIG. 1, parahydrogen can be a form of molecular hydrogen in which two or more protons are aligned antiparallel to each other. In some embodiments, parahydrogen may be formed in a gas form or in a liquid form. For example, in some embodiments, parahydrogen may be generated in gas form by flowing hydrogen gas through a chamber with a catalyst. In some embodiments, the hydrogen gas may be low in temperature. In some embodiments, the catalyst may be an inorganic catalyst such as iron oxide. In some embodiments, the hydrogen gas contains both parahydrogen and orthohydrogen, and the low temperature brings the hydrogen gas to thermodynamic equilibrium in the chamber, during which population of parahydrogen grows.

In some embodiments, the parahydrogen can be generated at a first location and subsequently transported to a second location for use. In some embodiments, a first location may be a chamber, which may be part of a container, bottle, holder or other regions capable of holding a gas or a liquid. Such chamber may be maintained at a suitable pressure or temperature. In some embodiments, the first location may refer to a physical location such as a room, a lab, a particular warehouse, hospital or other location where the parahydrogen may be generated.

In some embodiments, the generated parahydrogen may be transported in a chamber, which may be different from the chamber where the parahydrogen was generated. The chamber transporting the parahydrogen gas may be maintained at a suitable pressure or temperature, which may be transported by vehicle or persons. In some embodiments, transporting the parahydrogen may involve moving the parahydrogen from one container to a different container. In some embodiments, transporting the parahydrogen may involve moving the parahydrogen within a location, such as from one part of a room to another part of the room. In some embodiments, transporting the parahydrogen may involve moving the parahydrogen from one room in a building to a different room in the same building or to a nearby building. In some embodiments, transporting the parahydrogen may involve moving the parahydrogen to different locations in another part of the same city, or a different city. For example, transporting the parahydrogen may involve bringing the parahydrogen to a vicinity of a polarizer or an NMR/MRI device. In another example, in some embodiments, transporting the parahydrogen may involve packaging or shipping the parahydrogen in suitable containers as illustrated in FIG. 1.

Consistent with disclosed embodiments, the NMR material can be a target molecule. A precursor can include the target molecule. The precursor can be suitable for use in PHIP-SAH. The precursor can be mixed with parahydrogen in the presence of a hydrogenation catalyst to generate a parahydrogenated precursor. In various embodiments, the precursor may be combined with the parahydrogen to form a mixture. In some, embodiments the mixture may be formed by bubbling the parahydrogen gas into the mixture.

Consistent with disclosed embodiments, the precursor can include an unsaturated bond suitable for hydrogenation using the parahydrogen gas. Preferably, after bubbling the parahydrogen gas through, more than 50%, more than 80%, or almost all of the precursor may be parahydrogenated (e.g., creating the parahydrogenated precursor).

In some embodiments, the catalyst can be any molecule, complex or particle system that catalyzes hydrogenation. In some embodiments, a homogeneous metal catalyst such as a rhodium complex may be used for coordination and activation of target molecules and parahydrogen. In some embodiments, a rhodium complex is selected as the homogeneous metal catalyst. In some embodiments, a heterogeneous metal catalyst connected to a nanoparticle can be used for coordination and activation of the precursor and the parahydrogen.

As described herein, the precursor can include the target molecule and a sidearm. In some embodiments, the parahydrogen can hydrogenate the sidearm, generating a parahydrogenated sidearm. In various embodiments, the parahydrogen can hydrogenate the target molecule. In some embodiments, the hydrogenation may create Iz1Iz2 order, the lower energy state between $|\uparrow>|\downarrow>$, $|\downarrow>|\uparrow>$ or singlet spin order on two hydrogens spins.

Consistent with disclosed embodiments, a polarized precursor can be generated by applying at least one radio-frequency (RF) waveform to the parahydrogenated precursor to transfer polarization between the parahydrogen and a nuclear spin of the parahydrogenated precursor. In some embodiments, a polarized target molecule can be generated by transferring the spin order from the $^1$H spins in the parahydrogenated sidearm to a nuclear spin within the bound target molecule. In some embodiments, the polarized precursor can be hyperpolarized (e.g., can exhibit polarization when in a magnetic field in excess of a thermal equilibrium condition, such as a thermal equilibrium condition described by the Boltzmann distribution at the ambient temperature). Such hyperpolarization can include polarization of a nuclear spin (e.g., a $^{13}$C, $^{15}$N, or like nuclear spin) in excess of 5%, 10%, 20%, or 40% polarization.

Consistent with disclosed embodiments, at least one RF waveform can include a sequence of elements. An element in the sequence of elements can be a RF pulse. For example, an element in the sequence of elements can be an excitation pulse. An excitation pulse may be an RF pulse that modifies energy level or spin phase of a material (e.g., to increase the detectable polarization signal in the sample), such as a 90-degree (or approximately 90-degree pulse). An element in the sequence of elements can be a decoupling sequence. In some embodiments, a decoupling sequence can include one or more pulses, or one or more groups of RF pulses (e.g., described herein as a block of RF pulses, or pulse block).

In some embodiments, the at least one RF wave form may be generated by a waveform generator. The waveform generator may include one or more computing units, processors, controllers, associate memories, PCs, computers services, or any devices capable of carrying computational operations using inputs and producing outputs.

The at least one RF waveform can be applied to a sample including the parahydrogenated precursor. The at least one RF waveform can be applied to the sample using RF coils. The RF coils may have one or more channels. Such channels may be pathways for applying the RF signals to the sample.

There may be provided at least one channel for each different type of nuclear spin species. In some embodiments, there may be at least one proton ($^1$H) channel and at least one carbon-13 ($^{13}$C) channel. In some embodiments, the RF waveforms applied to the $^1$H channel and the $^{13}$C channel may differ. For example, the RF waveforms applied to the $^1$H channel and the $^{13}$C channel may differ. For example, an RF waveform for the $^1$H channel may include at least six elements (e.g., three iterations, each including an excitation pulse followed by a decoupling sequence). To continue this example, an RF waveform for the $^{13}$C channel may include at least three elements (e.g., an excitation pulse preceded by and followed by decoupling sequences). Optionally, the RF waveform for the $^{13}$C channel may further include an excitation pulse preceding the first decoupling sequence.

Various embodiments of the present disclosure describe applying a magnetic field having a strength of between 1 mT and 6000 mT. The magnetic field may be produced by an electro-magnet or a permanent magnet. The magnetic field may be applied to the sample in pulses or continuously (CW). The magnetic field may be static or time varying. The applied magnetic field may be spatially inhomogeneous. The inhomogeneity of the magnetic field can be characterized in parts per million (ppm) over a diameter of a spherical volume that holds the sample. In some embodiment, the magnetic field applied may have a spatial inhomogeneity across the volume of at least 1 ppm.

Consistent with disclosed embodiments, following polarization transfer, the polarized target molecule can be separated from the polarized precursor. In some embodiments, the polarized target molecule can be cleaved from the polarized precursor (e.g., from the parahydrogenated sidearm) using a chemical reaction. In this manner, the chemical reaction can produce the polarized target molecule as a reaction product. In some embodiments, the chemical reaction can be hydrolysis.

Consistent with disclosed embodiments, the polarized target molecule in the sample can be at least partially separated from the hydrogenation catalyst, cleaved parahydrogenated sidearms, or other reaction byproducts. In various embodiments, at least a fraction of the polarized target molecule can be extracted from the sample. In some embodiments, the fraction of the polarized target molecule can be extracted from the sample prior to or after separation of the hydrogenation catalyst, cleaved side arms, or other reaction byproducts form the sample. In some embodiments, such a separated fraction of the polarized target molecule may have at least a 100 mM concentration of the polarized target molecule. In some embodiments, such a separated fraction of the target molecules may have at least 5% polarization (e.g., at least 5%, 10%, 20%, or 40% polarization). Such a separated fraction may be suitable for use in an MRI scanner or an NMR probe.

Polarizing a Target Molecule

The disclosed embodiments can include methods implemented by disclosed systems for polarizing a target molecule, as described herein. The disclosed methods can include mixing, by a mixing mechanism, a solution including a precursor and a catalyst for hydrogenation. As described herein, the precursor can include a target molecule and a sidearm. A mixing mechanism may be a device for introducing, holding, and facilitating a blend, mixture, or solution of two or more materials. In some embodiments, the mixing mechanism may be disposed in a chamber, and the mixing may occur inside the chamber. In some embodiments, the solution may be mixed at a location away from the chamber. In some embodiments, the solution may be at least 100 µL in volume and may have a concentration of between 10 and 1000 millimolar (mM) (e.g., approximately 50 mM, 100 mM, 500 mM, or the like). In some embodiments, the mixing mechanism may be a gas-liquid exchange mechanism. For example, the gas-liquid exchange mechanism may be a bubbler or a diffusion system. In some embodiments, the mixing mechanism may comprise membranes adapted to permit diffusion of molecular hydrogen.

In some embodiments, a catalyst can be any molecule, complex or particle system that catalyzes hydrogenation. In some embodiment, there may be provided a homogeneous metal catalyst such as a rhodium complex. The rhodium complex can be used for coordination and activation of the precursor and parahydrogen. In some embodiments, a heterogeneous metal catalyst connected to a nanoparticle can be used.

In some embodiments, the parahydrogen may be formed in a gas form or in a liquid form. For example, in some embodiments, parahydrogen may be generated in gas form by flowing hydrogen gas through a chamber with a catalyst. In some embodiment, the hydrogen gas may be low in temperature. In some embodiment, the catalyst may be iron oxide. In some embodiments, the hydrogen gas can contain both parahydrogen and orthohydrogen, and the low temperature brings the hydrogen gas to thermodynamic equilibrium in the chamber, during which population of parahydrogen grows.

In some embodiments, polarization can be transferred from the parahydrogen to a nuclear spin of the target molecule, generating a polarized precursor. Following such polarization transfer, the solution may have at least 5% polarization (e.g., at least 5%, 10%, 20%, or 40% polarization). In some embodiments, the precursor may include an ester of pyruvate, and a parahydrogenated sidearm can be generated by hydrogenation of the sidearm at the site of an unsaturated carbon-carbon bond within the sidearm. In some embodiments, the polarization can be transferred to a nuclear spin on the pyruvate. In some embodiments, the parahydrogenated sidearm can be cleaved after the polarization transfer.

Various embodiments of the present disclosure disclose introducing the solution to a chamber configured to hold the solution during polarization transfer. In some embodiments, the solution may be mixed in the chamber. In some embodiments, the solution may be parahydrogenated in the chamber.

Various embodiments of the present disclosure disclose providing, by a radiofrequency wave form generator to a $^1H$ channel of one or more radiofrequency coils disposed around the chamber, a first RF waveform including at least two elements: an excitation pulse and a decoupling sequence. The decoupling sequence may include one or more pulse blocks, each pulse block including one or more dynamic decoupling pulses.

Various embodiments of the present disclosure describe providing, by a radiofrequency waveform generator to a $^{13}C$ channel of the one or more radiofrequency coils, a second RF waveform including at least two elements: an excitation pulse and a decoupling sequence. The decoupling sequence may include one or more pulse blocks, each pulse block including one or more dynamic decoupling pulses.

In some embodiments, the waveform generator may consist of one or more computing units, processors, controllers, associate memories, PCs, computers services, or any devices capable of carrying computational operations using inputs and producing outputs. In some embodiments, RF coils may radiate, or 'apply' the pulse sequences, including the first RF waveform. In some embodiments, the RF coils may have one or more channels. Channels may be pathways for RF signals. There may be provided at least one channel for each different type of NMR spectroscopy. In some embodiment, there may be at least one channel for $^1H$ and at least one channel for $^{13}C$.

In some embodiments, a first one of the set of at least ten dynamic decoupling pulses in the second pulse sequence may be synchronized with a first one of the at least ten dynamic decoupling pulses in a first iteration of the first pulse sequence. In some embodiments, a second one of the at least ten dynamic decoupling pulses in the second pulse sequence: may be preceded by an excitation pulse, the excitation pulse may be synchronized with the excitation degree pulse in a third iteration of the first pulse sequence, and may include a least ten dynamic decoupling pulses, and the least ten dynamic decoupling pulses may be synchronized with the least ten dynamic decoupling pulses in a third iteration of the first pulse sequence. In some embodiments, the excitation pulses may be 90-degree pulses.

In some embodiments, a third set of dynamic decoupling pulses in the second pulse sequence may include at least ten dynamic decoupling pulses, the least ten dynamic decoupling pulses may be offset synchronized with the least ten dynamic decoupling pulses in a second iteration of the first pulse sequence.

In some embodiments, the first, second and third set of decoupling pulses may have least 50, 100 or 200 pulses. In some embodiments, a mean time between each of the dynamic coupling pluses may be less than a proton relaxation time. In some embodiments, a median time between pulses in the pulse sequence may be less than a J-coupling between the protons divided by 100.

Various embodiments of the present disclosure disclose that the polarized target molecule may be at least partially separated from the hydrogenation catalyst using an extraction mechanism. In some embodiments, a fraction of the polarized target molecule can be extracted having a concentration of the hydrogenation catalyst less than 10 µM, 1 µM, 100 nM, 10 nM, 1 nM in the extracted fraction.

In some embodiments, the extraction mechanism may reduce the concentration of the hydrogenation catalyst, at least in part, by performing liquid-liquid separation of the hydrogenation catalyst into a first liquid, and the polarized target molecule (or, in some embodiments, the polarized precursor) into a second liquid. In some embodiments, the extraction mechanism may reduce the concentration the hydrogenation catalyst, at least in part, using a difference in binding affinities between the hydrogen catalyst and the polarized target molecule. In some embodiments, the extraction mechanism may reduce the concentration of the hydrogenation catalyst, at least in part, by mechanically separating the hydrogen catalyst from the polarized target molecule.

In some embodiments, the precursor may comprise an ester of pyruvate. In such embodiments, the polarized target molecule can be polarized pyruvate. The extraction mechanism can extract the pyruvate in a liquid-liquid extraction with aqueous, organic and/or fluorinated phases, such that the hydrogenation catalyst may be in the organic or fluorinated phase, and the pyruvate may be in the aqueous phase.

Various embodiments of the present disclosure disclose that a magnetic field with a strength between 100 mT and 5000 mT over the sample region within the chamber can be applied to the chamber at least during the provision of the first and second pulse sequences. The magnetic field may be produced by an electro-magnet or a permanent magnet. The magnetic field can be applied in pulses or continuously (CW). The magnetic field can be static or time varying. The magnetic field applied can be inhomogeneous (e.g., the magnetic field can exhibit non-uniformity). In some embodiments, the inhomogeneity of the magnetic field can be described in parts per million (ppm) over a diameter of a spherical volume. In some embodiments, the applied magnetic field can have an inhomogeneity of at least 1 ppm (or at least 5 ppm, 10 ppm, or 50 ppm). In some embodiments, the magnetic field may be produced by a Halbach magnet.

In some embodiments, the inhomogeneity of the applied magnetic field can be characterized in terms of a full width half maximum linewidth of $^1$H nuclear spins of the chamber after an excitation pulse. In some embodiments, the full width half maximum linewidth of $^1$H nuclear spins can be more than 100 Hz, 1 kHz, 4 kHz, or 10 kHz.

Precursors for PHIP-SAH Applications

Various embodiments of the present disclosure describe precursors including a target molecule and a sidearm. The sidearm can be parahydrogenated using parahydrogen (e.g., by mixing the precursor and the parahydrogen). In some embodiments, the hydrogenation may create Iz1Iz2 order, the lower energy state between $|\uparrow\rangle|\downarrow\rangle$, $|\downarrow\rangle|\uparrow\rangle$ or singlet spin order on two hydrogens spins, depending whether the hydrogenation is performed at a low magnetic field or high magnetic field.

In some embodiments, the precursor may be chosen such that (following the hydrogenation and other potential chemical reactions) the target molecule is suitable for use in HP MRI applications. In some embodiments, additional chemical reactions following hydrogenation can separate the target molecule from the precursor. Such additional chemical reactions may include cleaving of a side arm of the precursor, e.g., by hydrolysis. For example, the target molecule can be metabolite molecule, the precursor can be an ester of the metabolite molecule, and the target molecule can be polarized using the PHIP-SAH method. Following hydrogenation and polarization transfer, the ester may be hydrolyzed to produce a polarized target molecule.

In this invention, hydrolysis is defined as the cleavage of a molecule via a nucleophilic substitution reaction, with the addition of the elements of water. It can be also performed under anhydrous conditions under the presence of hydroxide ions.

Target Molecules for PHIP-SAH

Consistent with disclosed embodiments, enol or ynol esters of carboxylic acids can be used as precursors for PHIP-SAH. Advantageously, following hydrogenation of such esters, the two $^1$H spins exhibiting the spin order are only three and four bonds away from the closest carbon on the metabolite, which can be $^{13}$C enriched. Therefore, a high J coupling between the $^{13}$C spin and at least one of the $^1$H spins can be achieved, preferably larger than 1 Hz, 3 Hz, 5 Hz, thus enabling efficient polarization of the $^{13}$C spin. The vinyl ester of the carboxylic acids has the protons exhibiting the spin order with the same distance to the $^{13}$C, while other esters having a longer bond length, and therefore weaker coupling. However, for many molecules of interest, such as pyruvate, it can be difficult to synthesize the vinyl ester, and in many cases it is not stable. The enol and ynol ester molecules described herein exhibit the unsaturated bond at a distance from the $^{13}$C supporting high J coupling. The enol and ynol ester molecules can be used to synthesize the envisioned classes of precursors. As described herein, a precursor can include a target molecule and a sidearm. In some embodiments, some or all of the $^1$H atoms on the sidearm can be replaced by $^2$H or $^3$H atoms. In some embodiments, some or all of the $^1$H atoms on the precursor or target molecule can be replaced by $^2$H or $^3$H atoms. In some embodiments, "carbonyl" is referred to as (CO).

One aspect of the invention provides novel precursors, including compounds of Formulas I, II, IIa, IIb, IIc, III, IV, and V, tautomers thereof, deuterated derivatives of those compounds and their tautomers, salts thereof, and $^{13}$C enriched derivatives at one or more sites within the molecule which may be in turn subject to hyperpolarization, and the subsequent generation of precursors given by the general Formulas I, II, IIa, IIb, IIc, III, IV, and V.

Formula I encompasses the following structure

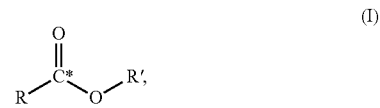

(I)

and includes tautomers thereof, deuterated derivatives of those compounds and their tautomers, pharmaceutically acceptable salts thereof, and $^{13}$C enriched derivatives at one or more sites, wherein:

C* denotes a carbon atom at the ester carbonyl center that is naturally $^{13}$C enriched or, optionally, a $^{13}$C labeled carboxylate carbon atom which can optionally undergo $^{13}$C hyperpolarization.

R is a linear, branched, or cyclic $C_1$-$C_{10}$ alkyl group, in which one or more C atoms maybe be replaced by CO, COOH, CH$_2$COOH, CONH$_2$, and R is optionally substituted with, one or more group(s) selected from a CO, an OH, an amino (NR$^1$R$^2$), a halogen atom(s), a halo-alkyl group(s), or a carbocycle, wherein the carbocycle is optionally substituted with an aliphatic or aromatic ring, which is optionally substituted by one or more functional groups. R' is a linear, branched or cyclic hydrocarbon $C_1$-$C_{10}$ alkyl group containing an unsaturated bond in a two-bond distance from C*, in which one or more C atoms maybe be replaced by CO, COOH, CH$_2$COOH, CONH$_2$, and R' is optionally substituted with, one or more functional group(s), selected from a halogen, a halo-alkyl group, and a carbocycle, wherein the carbocycle is optionally substituted with an aliphatic or aromatic ring, which is optionally substituted by one or more functional groups; R$^1$ and R$^2$ are each independently H, $^2$H, $^3$H or an amino protecting group, optionally selected from trifluoroacetyl, acetyl, benzoyl, carbobenzoxy, tert-butyl carbonate and benzyl.

In some embodiments, R is acetyl (H$_3$CCO), wherein the carbonyl carbon may be $^{13}$C.

Formula I also includes compounds of Formula II, where the R' group of Formula I comprises an alkene optionally substituted with an R$^3$, R$^4$, and R$^5$ substituents as shown in Formula II,

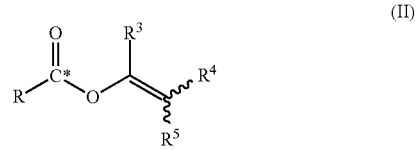

(II)

R$^3$, R$^4$, and R$^5$ are each independently H or a linear, branched, or cyclic $C_1$-$C_{10}$ alkyl hydrocarbon, wherein no more than two of the three of R$^3$, R$^4$, and R$^5$ may be a proton or deuterated species, thereof, wherein the hydrocarbon is optionally substituted with one or more group(s) selected from a $C_6$ aryl, benzyl, phenyl, heteroaryl, halogen, a haloalkyl, an optionally substituted carbocycle, and an optionally substituted heterocycle aryl or cycloalkyl groups, which is, each in its turn, optionally substituted by one or more functional groups selected from alkyl, alkoxy, or a heteroatom, such as N, O, Si, P, S, or a halogen, such as F, Cl, Br, I, that may also be further substituted.

For target molecules of Formula II, only one of the three substituents or two of the three substituents selected from $R^3$, $R^4$, and $R^5$ may be hydrogen.

In some embodiments, $R^5$ may be benzyl, phenyl, or a derivative, thereof.

Formula I also includes compounds of Formula III, wherein R' comprises an alkynyl group substituted with a terminal $R^6$ moiety consistent with formula (III):

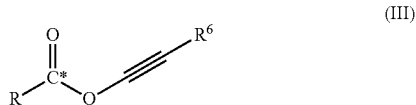

(III)

$R^6$ is H, or a linear, branched, or cyclic $C_1$-$C_{10}$ alkyl hydrocarbon, wherein the hydrocarbon is optionally substituted with one or more group(s) selected from a $C_6$-$C_{10}$ aryl, benzyl, phenyl, heteroaryl, halogen, a haloalkyl, an optionally substituted carbocycle, and an optionally substituted heterocycle aryl or cycloalkyl groups, which is, each in its turn, optionally substituted by one or more functional groups selected from alkyl, alkoxy, or a heteroatom, such as N, O, Si, P, S, or a halogen, such as F, Cl, Br, I, that may also be further substituted.

In preferred embodiments, the hydrogenation reaction of precursors of Formula II and Formula III may be parahydrogenated to form parahydrogenated esters of the Formula IV or Formula V:

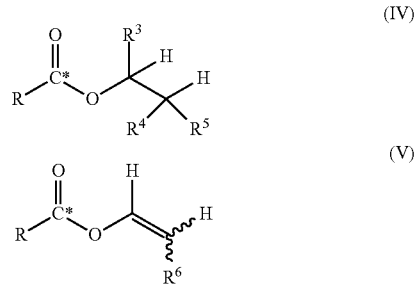

(IV)

(V)

The definitions of $R^3$, $R^4$, $R^5$, $R^6$ are defined as above for molecules (II), (III).

The definitions of $R^3$, $R^4$, $R^5$, $R^6$ are defined as above for molecules (III), (IV) wherein H may be an acceptable isotope such as $^2$H, and $^3$H.

Formula II also includes compounds of Formula IIa:

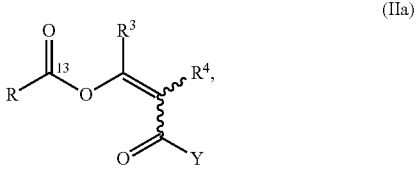

(IIa)

wherein, $R^3$ and $R^4$ are each independently H or a linear, branched, or cyclic $C_1$-$C_{10}$ alkyl hydrocarbon, wherein the hydrocarbon is optionally substituted with one or more group(s) selected from a $C_6$ aryl, benzyl, phenyl, heteroaryl, halogen, a haloalkyl, an optionally substituted carbocycle, and an optionally substituted heterocycle, which is, each in its turn, optionally substituted by one or more functional groups selected from alkyl, alkoxy, or a heteroatom, such as N, O, Si, P, S, or a halogen, such as F, Cl, Br, I, that may also be further substituted.

Y is selected from $R^x$, $OR^x$, $SR^x$, $NR^x_2$, or H wherein,
$R^x$ is selected from alkyl ($C_1$-$C_{10}$), cycloalkyl ($C_3$-$C_{18}$), aryl ($C_6$-$C_{10}$), or heteroaryl, H wherein one or more C atoms may be optionally substituted with alkyl ($C_1$-$C_6$), or aryl ($C_6$-$C_{10}$).

Formula II also includes compounds of Formula IIb:

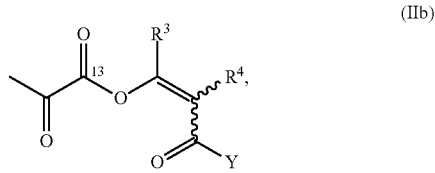

(IIb)

wherein,
$R^3$ and $R^4$ are independently selected from H, D, alkyl or cycloalkyl ($C_1$-$C_{10}$), aryl ($C_6$-$C_{10}$), or heteroaryl.

Y is selected from $R^x$, $OR^x$, $SR^x$, $NR^x_2$, or H wherein,
$R^x$ is selected from alkyl ($C_1$-$C_{10}$), cycloalkyl ($C_3$-$C_{18}$), aryl ($C_6$-$C_{10}$), or heteroaryl, H wherein one or more C atoms may be optionally substituted with alkyl ($C_1$-$C_6$), or aryl ($C_6$-$C_{10}$).

Formula II also includes compounds of Formula IIc:

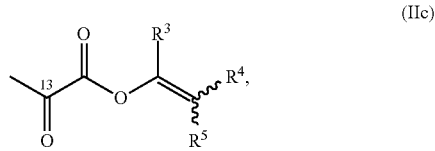

(IIc)

wherein,
$R^3$, $R^4$, and $R^5$ are independently selected from H, D, cycloalkyl ($C_1$-$C_{10}$), aryl ($C_6$-$C_{10}$), or heteroaryl.

General methods for characterization of precursors according to the formulae described included $^1$H and $^{13}$C NMR spectra were recorded on Bruker Avance 400 ($^1$H: 400.13 MHz; $^{13}$C: 100.62 MHz); δ values are reported in ppm and coupling constants are given in hertz (Hz). The signal of the solvent was used as an internal standard: $^1$H spectra: δ (CDCl$_3$)=7.26 ppm, δ (THF-d8)=1.72 ppm and 3.58 ppm; $^{13}$C spectra: δ (CDCl$_3$)=77.16 ppm, δ (THF-d8)=25.31 ppm and 67.21 ppm. The NMR spectra were measured at 298±2 K. The chemical structure of the synthesized compounds was verified via by means of HSQC and HMBC spectra. CDCl$_3$ and THF-d8 were purchased from Eurisotop.

One aspect of the invention includes methods to synthesize enol ester precursors. In some embodiments, enol esters of Formula II may be synthesized by O-Acylation of enolates. In some embodiments, the synthesis of enol esters of Formula II may be synthesized by the addition of a carboxylic acid to a terminal or internal alkyne.

Example 1: Addition of a Compound of Formula I to an Alkyne to Form a Derivative Compound of Formula II

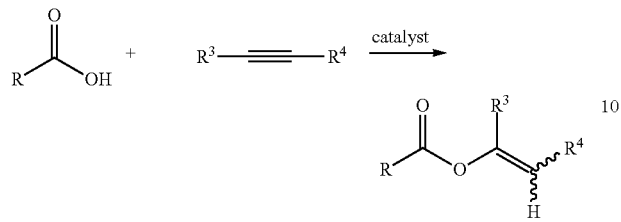

This reaction may be performed under homogeneous catalysis by a transition metal complex using an organometallic catalyst such as an iridium catalyst or in preferred embodiments, conducting transition metal catalysis using a ruthenium catalyst. In some embodiments this results in a metalated intermediate enol ester, that can be converted into the enol ester of Formula II.

In another embodiment, synthesis of precursors of Formula II require the transfer of an optionally substituted vinyl group of an enol ester to a carboxylic acid. This synthesis, known in the art as transesterification may be carried out under homogeneous catalysis in the presence of a transition metal.

In some embodiments, the synthesis of an enol ester of Formula II may be afforded by the allyl-vinyl-isomerization of an allyl ester. The process of allyl-vinyl-isomerization may be carried out under the presence of a transition metal catalyst.

In some embodiments, the synthesis of an enol ester of Formula II may be afforded by the O-acylation of an enolate. In preferred embodiments, the carboxylic acid of interest may require conversion to a reactive intermediate such as an acyl halide, an anhydride or a mixed anhydride (e.g. RCOO—POCl$_2$, RCOO—SO$_2$CF$_3$, . . . ).

In certain embodiments, the ester or ester derivative of the carboxylic acid includes the manipulation of additional functional groups belonging to the precursors of Formula I. In some embodiments, precursors of Formula II, IIa, IIb, IIc, III may undergo hydrolysis to form precursors of Formula I.

Consistent with disclosed embodiments, suitable precursors for introduction into PHIP-SAH can include vinyl esters, such as vinyl acetate.

Conventional techniques for preparing vinyl esters from a carboxylic acid (e.g., esterification by condensation of the acid with vinyl alcohol) have not been successfully demonstrated for a wide class of compounds, potentially due to vinyl alcohol being the non-favorable form of acetaldehyde (e.g., the oxygen may have poor donor reactivity).

In one synthetic approach, suitable vinyl pyruvate-type precursors may be synthesized starting from pyruvic acid. This alternative approach can include the addition of a carboxylic acid to acetylene or an acetylene-derivative:

Example 2: Synthesis of (Z)-Styryl 2-oxopropanoate

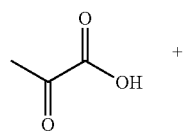

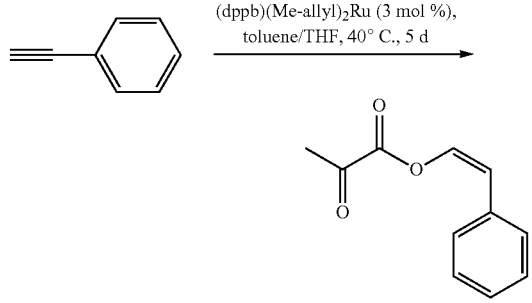

Bis(2-methylallyl)-(bis(diphenylphosphino)-butane)-ruthenium (200 mg, 0.314 mmol) was mixed with dry and degassed toluene (8.0 mL) and heated to 40° C. At this temperature, a solution of freshly distilled pyruvic acid (700 µL, 9.93 mmol) and phenylacetylene (1091 µL, 9.93 mmol) in a mixture of dry toluene (2.0 mL) and dry tetrahydrofuran (120 µL) was added under stirring over a period of 16 hours by means of a syringe pump. After 48 hours, another amount of pyruvic acid (490 µL, 6.95 mmol) was added and the reaction was maintained at 40° C. for an additional 72 hours. After cooling to 20° C., a dark oil separated and the orange upper liquid was decanted, collected and concentrated at 0.02 mbar. For further purification, the oily residue was dissolved in dry dichloromethane (1.0 mL), transferred into a small glass which was put into a larger glass filled with n-pentane (10 mL). The sealed system was put into a fridge (4° C.) for three days, whereupon a dark oil separated in the small glass. The upper yellow liquid in the small glass was collected and concentrated at 0.02 mbar which yielded (Z)-styryl pyruvate (668 mg, 3.51 mmol, 35%) as a yellow oil. $^1$H NMR (400 MHz, CDCl$_3$): δ [ppm]=2.59 (s, 3H, CH$_3$), 5.93 (d, $^3J_{H,H}$=7.1 Hz, 1H, C=CH), 7.28-7.36 (m, 2H, H$_{Ph}$ and C=CH), 7.38-7.45 (m, 2H, H$_{Ph}$), 7.67-7.72 (m, 2H, H$_{Ph}$); $^{13}$C NMR (101 MHz, CDCl$_3$): δ [ppm]=26.7 (CH$_3$), 115.3 (C=C), 128.1 (C$_{Ph}$), 128.7 (C$_{Ph}$), 129.7 (C$_{Ph}$), 132.9 (C=C), 133.2 (C$_{Ph}$), 157.0 (COO), 190.0 (C=O).

Example 3: Synthesis of 13C-enriched (Z)-Styryl 2-oxopropanoate

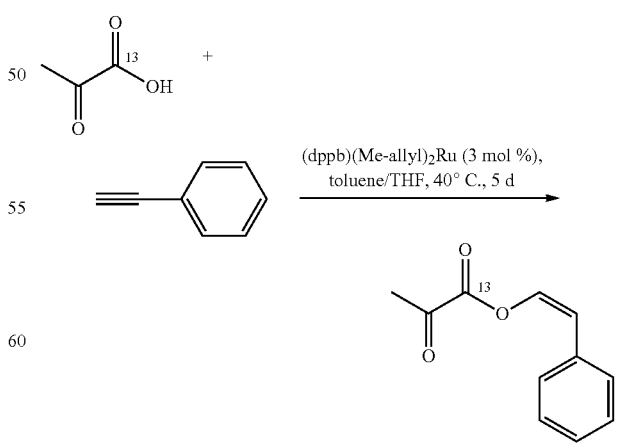

Synthesis of $^{13}$C-enriched (Z)-Styryl 2-oxopropanoate can be envisioned to undergo the same synthetic protocol described in the previous example using $^{13}$C-enriched pyruvic acid obtained, commercially.

Example 4: Synthesis of vinyl ester pyruvate derivative, (E)-2-Bromo-1-(4-methoxyphenyl)-2-(triisopropylsilyl)vinyl-2-oxopropanoate

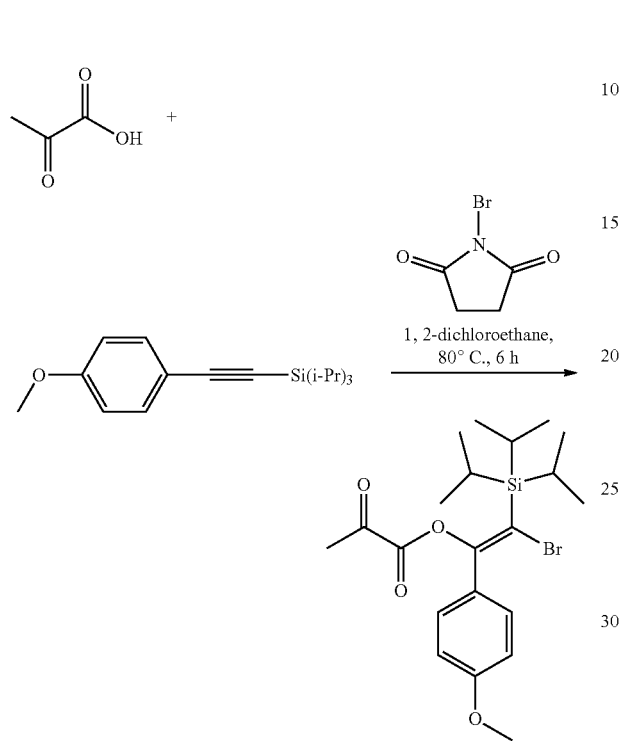

Triisopropyl((4-methoxyphenyl)ethynyl)silane (288 mg, 1.0 mmol) and N-bromosuccinimide (320 mg, 1.80 mmol) were suspended in dry 1,2-dichloroethane (5.0 mL). Freshly distilled pyruvic acid (127 μL, 1.80 mmol) was added and the mixture was stirred at 80° C. for six hours. Thereafter, the reaction was quenched by the addition of 10% aqueous sodium thiosulfate solution (20.0 mL) and the mixture was extracted with ethyl acetate (3*20 mL). The organic extracts were collected and dried over anhydrous sodium sulfate. After removing the volatile components, the residue was purified via flash chromatography (eluent: CHCl$_3$). The enol ester (266 mg, 58%) was isolated as a colorless solid. $^1$H NMR (400 MHz, CDCl$_3$): δ [ppm]=1.02-1.03 (m, 21H, Si(iPr)$_3$), 2.50 (s, 3H, CH$_3$), 3.81 (s, 3H, OCH$_3$), 6.82-6.84 (m, 2H, H$_{Ph}$), 7.40-7.42 (m, 2H, H$_{Ph}$); $^{13}$C NMR (101 MHz, CDCl$_3$): δ [ppm]=12.5 (SiCH), 18.9 (CH$_3$, Si(iPr)$_3$), 26.9 (CH$_3$), 55.5 (OCH$_3$), 113.4 (C$_{aryl}$), 116.5 (C=C), 126.4 (C$_{aryl}$), 131.9 (C$_{aryl}$), 154.4 (O—C=C), 157.3 (COO), 161.0 (C$_{aryl}$), 191.0 (C=O).

Example 5: Synthesis of 13C-Enriched Vinyl Ester Pyruvate Derivative, (E)-2-Bromo-1-(4-methoxyphenyl)-2-(triisopropylsilyl)vinyl-2-oxopropanoate

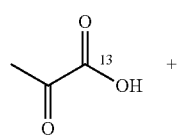

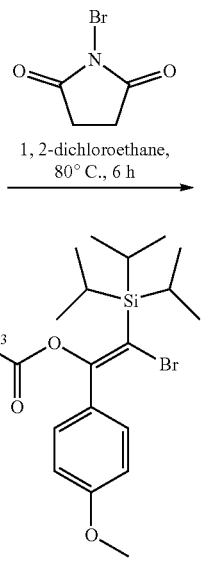

Synthesis of $^{13}$C-enriched (E)-2-Bromo-1-(4-methoxyphenyl)-2-(triisopropylsilyl)vinyl-2-oxopropanoate can be envisioned to undergo the same synthetic protocol described in the previous example using $^{13}$C-enriched pyruvic acid obtained, commercially.

Example 6: Synthesis of (Z)-3-oxobut-1-en-1-yl 2-oxopropanoate Through O-Acylation of Enolates with Pyruvoyl Chloride

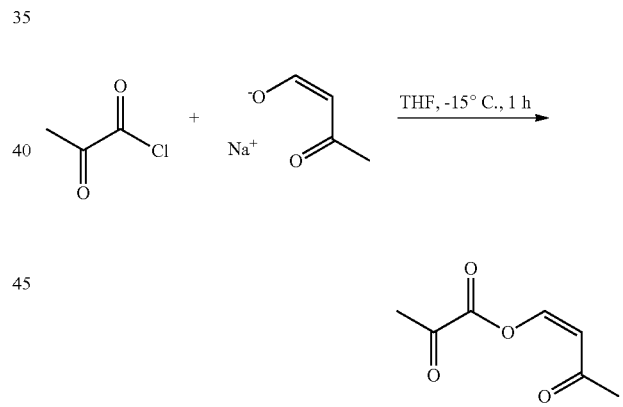

Sodium (Z)-3-oxobut-1-en-1-olate (1.08 g, 10.0 mmol) was suspended in dry tetrahydrofuran (30 mL) and cooled to −15° C. Under vigorous stirring, pyruvoyl chloride (1.07 g, 10.0 mmol) was added dropwise over a period of five minutes. After stirring for one hour at this temperature, the volatile components were removed at 0.1 mbar and the residue was distilled to give (Z)-3-oxobut-1-en-1-yl 2-oxopropanoate (1.25 g, 8.0 mmol, 80%) as a colourless liquid.

$^1$H NMR (400 MHz, THF-d8): δ [ppm]=2.12 (s, 3H, CH$_3$, sidearm), 2.36 (s, 3H, CH$_3$, pyruvate), 6.04 (d, $^3J_{H,H}$=12.7 Hz, 1H, C=CH), 8.00 (d, $^3J_{H,H}$=12.7 Hz, 1H, C=CH); $^{13}$C NMR (101 MHz, THF-d8): δ [ppm]=25.81 (CH$_3$, pyruvate), 27.43 (CH$_3$, sidearm), 116.85 (OC=CH), 147.61 (OC=CH), 155.95 (COO), 188.28 (C=O, pyruvate), 196.27 (C=O, pyruvate).

Example 7: Synthesis of 13C-enriched (Z)-3-oxobut-1-en-1-yl 2-oxopropanoate Through O-Acylation of Enolate Species with 13C-Enriched Pyruvoyl Chloride

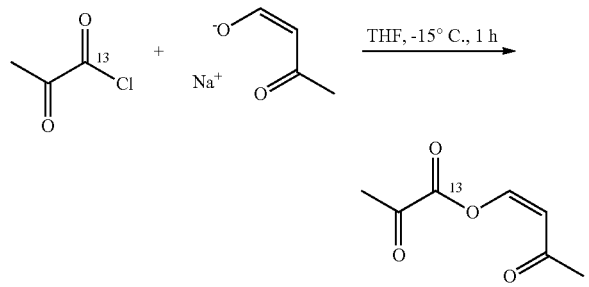

Synthesis of $^{13}$C-enriched (Z)-3-oxobut-1-en-1-yl 2-oxopropanoate can be envisioned to undergo the same synthetic protocol described in the previous example using $^{13}$C-enriched pyruvoyl chloride obtained, commercially.

Example 8: Parahydrogenation of Exemplary Precursor

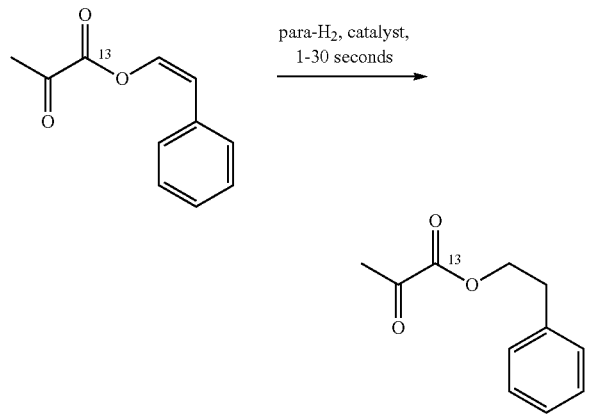

Parahydroenation of precursor molecules of Formulae II, IIa, IIb, and IIc, can be envisioned according to the protocol of Example 8, wherein the unsaturated enolic bond of the sidearm may undergo hydrogenation in the presence of a catalyst to afford a parahydrogenated precursor.

Example 9: Cleavage of Exemplary Precursors after Parahydrogenation

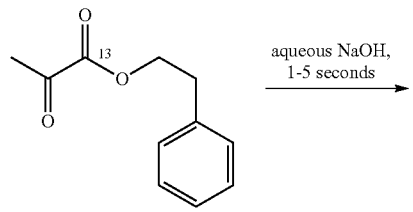

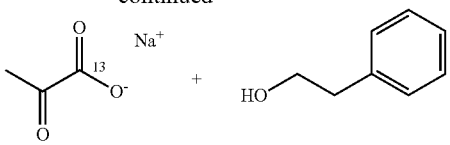

After hydrogenation of precursor molecules of Formulae II, IIa, IIb, and IIc, the parahydrogenated ester may be cleaved by the addition of sodium hydroxide solution into the target carboxylate and the parahydrogenated sidearm.

System for Generating Polarized Material

Consistent with disclosed embodiments a radiofrequency waveform generator can be coupled to one or more radiofrequency coils. In some embodiments, the wave form generator may consist of one or more computing units, processors, controllers, associate memories, PCs, computers services, or any devices capable of carrying computational operations using inputs and producing outputs. In some embodiments, RF coils may radiate, or 'apply' the pulse sequences, including the first pulse sequence. In some embodiments, the RF coils may have one or more channels. Channels may be pathways for RF signals. There may be provided at least one channel for each different type of NMR spectroscopy. In some embodiment, there may be at least one channel for $^1$H and at least one channel for $^{13}$C. An excitation pulse may be an RF pulse that modifies energy level or spin phase of a material. In some embodiments, the RF coils may be disposed around a chamber, a volume of the chamber disposed within the RF coils may be between 1 ml and 60 ml.

Various embodiments of the present disclosure disclose a memory storing instructions. A memory may be any information storage unit, such as volatile or non-volatile memory storage unit, such as DRAM (SDRAM, DDR, GDDR), SRAM, ROM, flash memory, magnetic memory storage (tape, hard disk), and/or optical memory storage. Instructions may be software module, codes, algorithms, machine instructions, formulas, or any forms of data that may be used to generate RF pulses when executed by at least one processor of the system.

Various embodiments of the present disclosure disclose providing, by the radiofrequency wave form generator to a $^1$H channel of the one or more radiofrequency coils, a first pulse sequence including at least one excitation pulse, and at least one set of a least ten dynamic decoupling pulses. Consistent with disclosed embodiments, the radiofrequency wave form generator can provide, to a $^{13}$C channel of the one or more radiofrequency coils, a second pulse sequence including at least one excitation pulse, and at least one set of a least ten dynamic decoupling pulses.

In some embodiments, a mean time between the dynamic coupling pulses may be less than the $^1$H spin-echo coherence time of the molecule in the polarizer. In some embodiments, the set of at least ten dynamic decoupling pulses may comprise at least 50, 100, or 200 dynamic decoupling pulses. In some embodiments, a median time between pulses in the RF waveform may be less than the inverse of the J-coupling between the protons divided by 20-2000. In some embodiments, the pulses in the dynamical decoupling sequence include at least two pulses with different phases with a time interval of at least 10 μs between each of the at least two pulses. In some embodiments, the pulses in the dynamical decoupling sequence include pulses with a non-rectangular shape. For example, a non-rectangular shape pulse shape can be determined to provide decoupling in an inhomogeneous magnetic field.

Consistent with disclosed embodiments, a magnetic field source can be disposed around the chamber. In some embodiments, the magnetic field source may be configured to generate a magnetic field with the chamber having a field strength, at least within the sample region of between 1 mT and 6000 mT. In some embodiments, the magnetic field may be applied to the chamber at least during the provision of the first and second pulse sequences. The magnetic field may be produced by an electro-magnet or a permanent magnet. The magnetic field may be provided intermittently or continuously (CW). The magnetic field may be static or time varying. The magnetic field may be inhomogeneous. In some embodiments, the inhomogeneity may be described in parts per million (ppm) over a diameter of a spherical volume. In some embodiments, a degree of inhomogeneity of the magnetic field may exceed a threshold value. The threshold value may be at least 1 ppm. In some embodiments, the threshold value may be at least 100 ppm, 300 ppm, or 1000 ppm. In some embodiments, the magnetic field may be produced by a permanent magnet, such as a Halbach magnet array.

A degree of inhomogeneity of the applied magnetic field may be alternatively or additionally expressed as a full width half maximum linewidth of $^1$H nuclear spins following an excitation pulse. In some embodiments, so expressed, the degree of inhomogeneity of the applied magnetic field may be greater than 100 Hz, greater than 1 kHz, greater than 4 kHz, or greater than 10 kHz.

Various embodiments of the present disclosure disclose a mixing mechanism. The mixing mechanism may be a device for introducing, holding, and facilitating a blend, mixture, or solution of two or more materials. In some embodiments, the mix mechanism may be configured to mix parahydrogen gas with a solution containing a precursor, which can include a target molecule and a sidearm. In some embodiments, the mixing mechanism may be disposed in a chamber, and the mixing may occur inside the chamber. In some embodiments, the solution may be mixed at a location away from the chamber. In some embodiments, the solution may be at least 100 μL in volume and may have a concentration of between 10 and 1000 millimolar (mM) (e.g., approximately 50 mM, 100 mM, 500 mM, or the like). In some embodiments, the mixing mechanism may be a gas-liquid exchange mechanism. For example, the gas-liquid exchange mechanism may be a bubbler or a diffusion system. In some embodiments, the mixing mechanism may comprise membranes adapted to permit diffusion of molecular hydrogen.

Various embodiments of the present disclosure disclose an extraction mechanism. In some embodiments, the extraction mechanism may comprise a purifier. In some embodiments, the extraction mechanism may reduce the concentration the hydrogenation catalyst, at least in part, by performing liquid-liquid separation of the hydrogenation catalyst into a first liquid, and the polarized material into a second liquid. In some embodiments, the extraction mechanism may reduce the concentration the hydrogenation catalyst, at least in part, using a difference in binding affinities between the hydrogen catalyst and the parahydrogenated target molecules. In some embodiments, the extraction mechanism may reduce the concentration the hydrogenation catalyst, at least in part, by mechanically separating the hydrogen catalyst from the parahydrogenated precursor.

In some embodiments, there may be provided that the first pulse sequence includes at least three iterations of an excitation pulse, each iteration of the excitation pulse followed by a set of a least ten dynamic decoupling pulses. In some embodiments, there may be provided that the second pulse sequence includes at least two sets of dynamic decoupling pulses. In some embodiments, the excitation pulse may be a 90-degree pulse.

Application to HP MRI and Metabolic Applications

Consistent with disclosed embodiments, PHIP can be used to produce polarizing metabolites for HP MRI. Such production methods can provide improvements in throughput and reductions in cost, as compared to conventional methods.

FIG. 1 illustrates a process for PHIP polarization, which may be large-scale PHIP polarization for in vitro and in vivo HP MRI. In step 101, parahydrogen can be generated by flowing cold hydrogen gas through a chamber with a catalyst (e.g., iron oxide or another suitable catalyst), bringing the parahydrogen and orthohydrogen to their thermodynamic equilibrium. In some embodiments, at low temperatures, parahydrogen may be increasingly populated. In some alternative embodiments, liquid parahydrogen may be prepared similarly. In step 103, parahydrogen can be transported to a suitable location (e.g., proximate to MRI scanners). As depicted, the parahydrogen can be transported in suitable containers, such as gas bottles. In some alternative embodiment, the pressurized parahydrogen may be liquid parahydrogen bottles, which may also be filled and shipped. In step 105, a mixture of precursor molecules and hydrogenation catalysts can then be prepared. In some embodiments, gaseous parahydrogen may be bubbled into the mixture, hydrogenating the precursor molecules (e.g., generating parahydrogenated precursor molecules) and creating Iz1Iz2, the lower energy state between $|\uparrow\rangle|\downarrow\rangle$, $|\downarrow\rangle|\uparrow\rangle$ or singlet spin order on two hydrogens spins. In step 105, a sequence of RF pulses may then be used to transfer the spin order to a net magnetization on a nuclear spin of choice on the parahydrogenated precursor molecules (e.g., generating polarized precursor molecules). In step 107, the polarized precursor molecules may be then separated from the catalysts. In a preferred embodiment, the precursor to be parahydrogenated and polarized may include a sidearm (e.g., the precursor can be an ester of the target molecule). The hydrogenation reaction can occur at the sidearm, and the spin order may be transferred to polarization on a nuclear spin in the target molecule (e.g., generating polarized target molecules). In some embodiments, in a separation step 109, the sidearm may be cleaved, with the sidearm residues potentially separated as well from the polarized target molecules. In step 111, after adapting the solution containing the polarized target molecules for injection (e.g., by regulating temperature, pH, or other relevant characteristics) at least a portion of the solution containing polarized molecule may be injected into a patient for a hyperpolarized MRI experiment.

FIG. 2 provides additional details of the PHIP-SAH process, consistent with disclosed embodiments. As depicted in FIG. 2, the process comprises parahydrogenation of precursor molecules, transfer of polarization to a target molecule, and cleavage and separation of the sidearm.

In step 201, precursor molecules can be parahydrogenated. Consistent with disclosed embodiments, the precursor molecules can be parahydrogenated using a hydrogenation catalyst. The hydrogenation catalyst can be any molecule, complex or particle system that catalyzes hydrogenation. In some embodiments, a homogeneous metal catalyst such as a rhodium complex may be used for coordination and activation of precursor molecules and parahydrogen. In some other embodiments, a heterogeneous metal catalyst connected to a nanoparticle may be used as the catalyst.

Consistent with disclosed embodiments, the precursor molecules may be molecules with an unsaturated bond that can be parahydrogenated by the parahydrogen gas. In some embodiments, after bubbling the parahydrogen gas through, more than 50%, more than 80% or almost all of the molecules may be parahydrogenated.

In steps 203 and 205, polarization can be transferred to a nuclear spin, polarizing the precursor molecules. Consistent with disclosed embodiments, PHIP may include the transfer of the Iz1Iz2 or singlet spin order to polarization on the nuclear spin of choice in the parahydrogenated precursor. In step 203, a singlet spin order (or minimally IzIz order) can be transferred to the sidearm. In step 205, an RF pulse sequence can be used to transfer the polarization to a $^{13}C$ spin in the target molecule of the parahydrogenated precursor. In high magnetic fields, e.g. 1 mT or above, the spin order may be transferred to polarization by a sequence of RF pulses on resonance with the $^1H$ and the nuclear spin species of interest. In some embodiments, this may be performed in an NMR/MRI spectrometer enabling spectral resolution.

Achieving high polarization using PHIP in high concentrations in a high magnetic field may be difficult, in part because of radiation damping due to the very large oscillating RF signal generated by the polarized protons. In some embodiments, such radiation damping may be addressed by having a proton full width at half maximum (FWHM) of about 100 Hz, 400 Hz, 1 kHz, 4 kHz or larger, corresponding to a relatively short T2*. As the radiation damping may be inversely proportional to the proton T2*, this may significantly reduce the effect of radiation damping. However, it has been shown that when increasing the proton inhomogeneity above 1-5 ppm in magnetic fields 1T and above, polarization transfer protocols known in the prior art do not perform sufficiently well and the achievable polarization on the $^{13}C$ nuclear spins is reduced.

Several outstanding challenges are present in the state of the art, which may prevent scaling up the polarization to larger volumes or concentrations:

Generating magnetic fields of 100 mT or larger, with less than 5 ppm homogeneity, may be difficult to achieve. Hence such fields are typically produced in small volumes (such as less than 1 ml). In larger volumes, such as greater than 1 ml, producing such homogeneous field is a major engineering challenge, typically requiring massive and potentially expensive superconducting magnets as well as active shimming.

Scaling up volume increases radiation damping. Therefore, while 1 ppm inhomogeneity may be sufficient for polarizing a concentration of 50 mM in 0.6 ml volume, the same concentration in a larger volume would drastically reduce polarization due to radiation damping.

Increasing the proton inhomogeneity above 1-5 ppm in magnetic fields 1T and above may be difficult to achieve with known transfer protocol. Known polarization transfer protocols do not perform sufficiently, and the achievable polarization on the $^{13}C$ nuclear spins may thus be reduced significantly.

In step 207, polarized target molecules can be separated from the polarized precursors. The precursor molecules may be chosen so that following the hydrogenation, and potentially additional chemical reactions, one of the products may be the polarized target molecules for use in the HP MRI experiments. In some embodiments, an additional chemical reaction following the hydrogenation may include cleaving of a sidearm, e.g. by hydrolysis. For example, in some preferred embodiments, the precursor can be an ester of the target molecule (which can be, for example, a metabolite). In this manner, the target molecule can be polarized using the PHIP-SAH method. In some embodiments, the ester may be rapidly cleaved following the polarization transfer, thus producing the polarized target molecule (e.g., the polarized metabolite) as a product. For example, many esters of metabolites may be used as precursor molecules. In some embodiments, in which the target molecule may be pyruvate, vinyl pyruvate, cinnamyl pyruvate, allyl pyruvate and propargyl pyruvate may be used as the precursor.

Various embodiments of the present disclosure disclose a polarizer of NMR materials capable of achieving hyperpolarization of $^{13}C$ or $^{15}N$ spins in an NMR materials in volumes of greater than 10 ml, 30 ml, or 50 ml within three minutes. Such a polarizer can be a PHIP polarizer capable of achieving such high polarization in polarized precursor molecules (or in polarized target molecules following cleavage). Various embodiments of the present disclosure disclose that in an inhomogeneous magnetic field with inhomogeneity of greater than 1 ppm, 5 ppm, 10 ppm, 50 ppm, 100 ppm, and/or 500 ppm a field of between 1 mT and 6000 mT, with novel polarization transfer sequences, may overcome the adverse effects of the high inhomogeneities level.

Setup for Large Volume PHIP Polarizer

Figure 3:
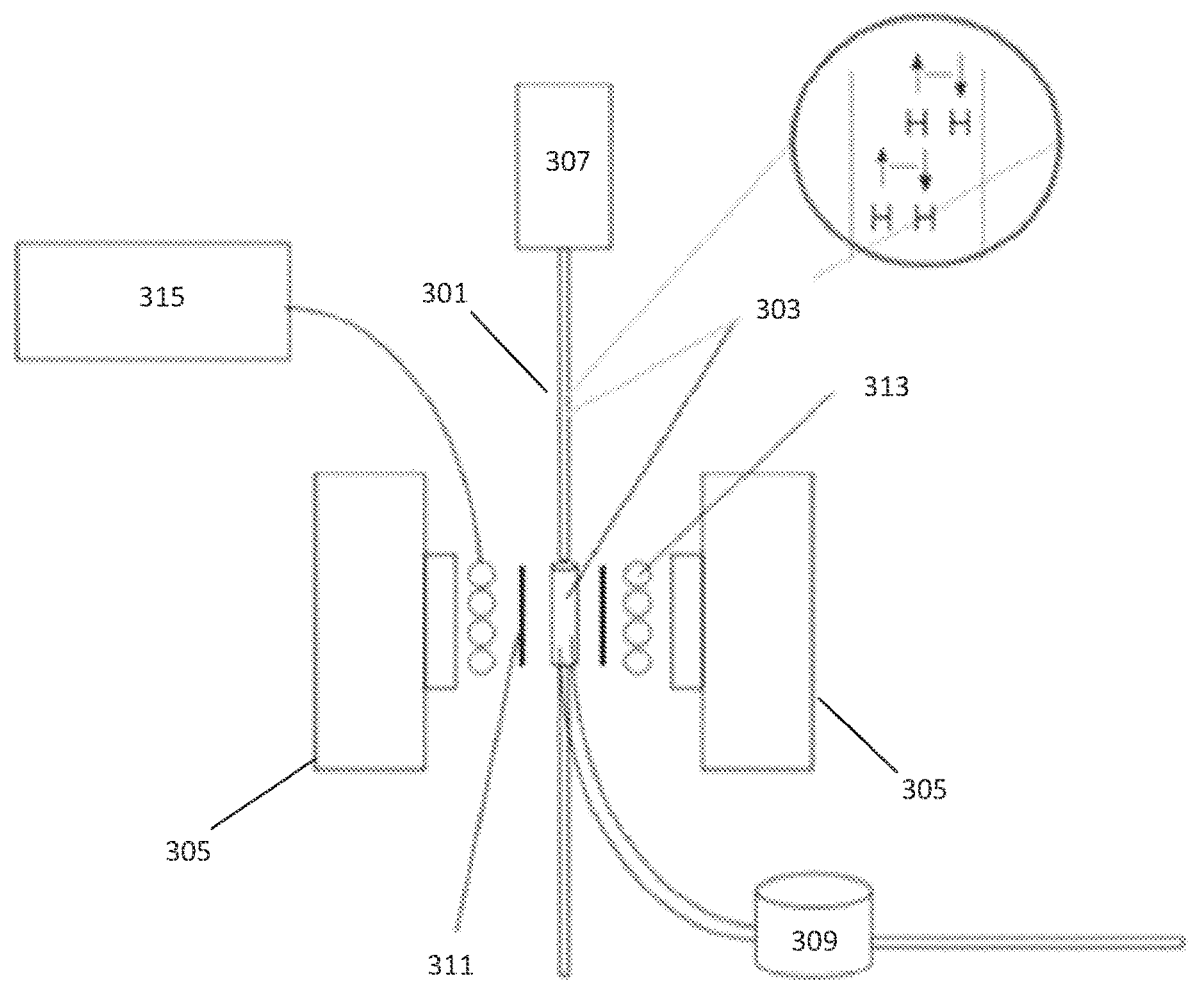
FIG. 3 illustrates an overview of components of PHIP polarizer with inhomogeneous field, in accordance with disclosed embodiments.

FIG. 3 depicts the overview of the setup and components of PHIP polarizer with inhomogeneous field, consistent with disclosed embodiments. In some embodiments, the PHIP polarizer can include a PHIP cavity 303, magnet 305, a parahydrogen reservoir 307, an extraction and purification chamber 309, heating elements 311, an RF generator 315, and an RF coil 313. In some embodiments, one or more of these components may be omitted (e.g., the parahydrogen dissolution component, the extraction and purification chamber 309, or the like).

Consistent with disclosed embodiments, the magnet 305 may be configured to produce a magnetic field. In some preferred embodiments, magnet 305 has a mean magnetic field strength between 1 mT and 6000 mT and a magnetic field inhomogeneity of no less than 10 ppm and no more than 1000 ppm over a volume of 1 ml, 5 ml, 10 ml, 30 ml, or 60 ml (e.g., within PHIP cavity 303, within a predetermined region of PHIP cavity 303 configured for polarizing a sample, or the like). In some embodiments, the mean magnetic field can be between 100 and 500 mT or between 100 and 5000 mT. In some embodiments, the magnetic field inhomogeneity over the volume of the sample can be between 1 and 250 microtesla (µT), or between 7 µT and 25 µT, or between 7 µT and 50 µT. In some preferred embodiments, magnet 305 may be an electromagnet, a permanent magnet, or an array of permanent magnets. In some embodiments, magnet 305 may produce the magnetic field having the afore-mentioned inhomogeneity without active shimming. In some embodiments, the magnetic field source can be a non-superconducting magnet and the mean magnetic field strength can be between 100 and 2500 mT.

Consistent with disclosed embodiments, the PHIP cavity 303 can be configured to house the sample. In some embodiments, parahydrogen may be bubbled into the sample in PHIP cavity 303 through gas transport line 301 (e.g., connected to parahydrogen reservoir 307). In this manner, PHIP cavity 303 can serve as a parahydrogen dissolution component for parahydrogenation of the precursor. An RF generator 315 may produces RF pulses to excite the sample through RF coil 313. In some embodiments, RF coil 313 forms an RF cavity, in which sample may be radiated by the RF pulses from RF coil 313. In some preferred embodiments, RF cavity may be the PHIP cavity 303. In other embodiments, PHIP cavity 303 may be distinct from RF cavity (i.e. parahydrogen bubbling may occur outside RF cavity, and possibly outside the magnetic field). The sequence for the polarization transfer may be in form of RF radiation. In some preferred embodiments, in order to produce envisioned sequences for the polarization transfer, RF generator 315 may include an arbitrary waveform generator (AWG). In some preferred embodiments, RF coil 313 may be connected to an NMR probe for performing NMR measurements. Even in the case that due to the inhomogeneous field, where NMR measurements may not result in spectroscopic quality, such NMR measurements may still be used for monitoring and quality control of the polarization. Heating elements 311 may be configured to control the temperature inside PHIP cavity 303. For example, for improved hydrogenation, the sample temperature may be raised to above a predetermined temperature between 40° C. and 100° C. (e.g., above 40° C., above 60° C., above 80° C., or above 100° C.).

Following polarization transfer, the sample may be transported to the extraction and purification system 309. Consistent with disclosed embodiments, extraction and purification system 309 can separate the polarized target molecules (or in some embodiments the polarized precursor molecules) from the catalysts and organic solvent used for the hydrogenation. In some embodiments, extraction and purification system 309 can be configured to perform a liquid-liquid extraction between an organic phase and an aqueous phase to separate the polarized target molecules (or in some embodiments the polarized precursor molecules) from the catalysts and organic solvent. In some embodiments, a fluorinated phase may be used in addition to/in alternative of the organic phase. The fluorinated phase may be combined with the aqueous phase for improved separation. In some embodiments, the polarized precursor molecules may be cleaved to produce the polarized target molecules inside at least one of the RF cavity or the extraction and purification system 309. In some embodiments, pH level and temperature of the sample may be monitored and controlled in extraction and purification system 309 in order to meet conditions for injection into the patient.

In some preferred embodiments, extraction and purification system 309 can be configured to perform a purification step. The purification step can reduce the concentration of the hydrogenation catalyst reduced from the 0.1-100 mM range to less than 1 µM. In some embodiments, the purification step can include liquid-liquid separation as described herein. In some other embodiments, purification step may include adding a binding material which binds preferentially to the catalyst, with which the binding material may be then separated by filtration, centrifugation, or other mechanical means.

In some embodiments, the hydrogenation of precursor molecules, polarization transfer, and optional extraction and purification steps may be performed repeatedly in a predetermined time period. In some embodiments, the predetermined time period may be within a relaxation time of the nuclear spin of interest. In some embodiments, the hydrogenation and polarization transfer steps may be performed rapidly (e.g., less than 1 second, 10 seconds, or another suitable number depending on the relaxation time of the nuclear spin of interest) to enable polarization of a larger volume of material. In some embodiments, these steps may be performed in a continuous flow system. In some other embodiments, these steps may be performed in several discrete steps.

Figure 4:
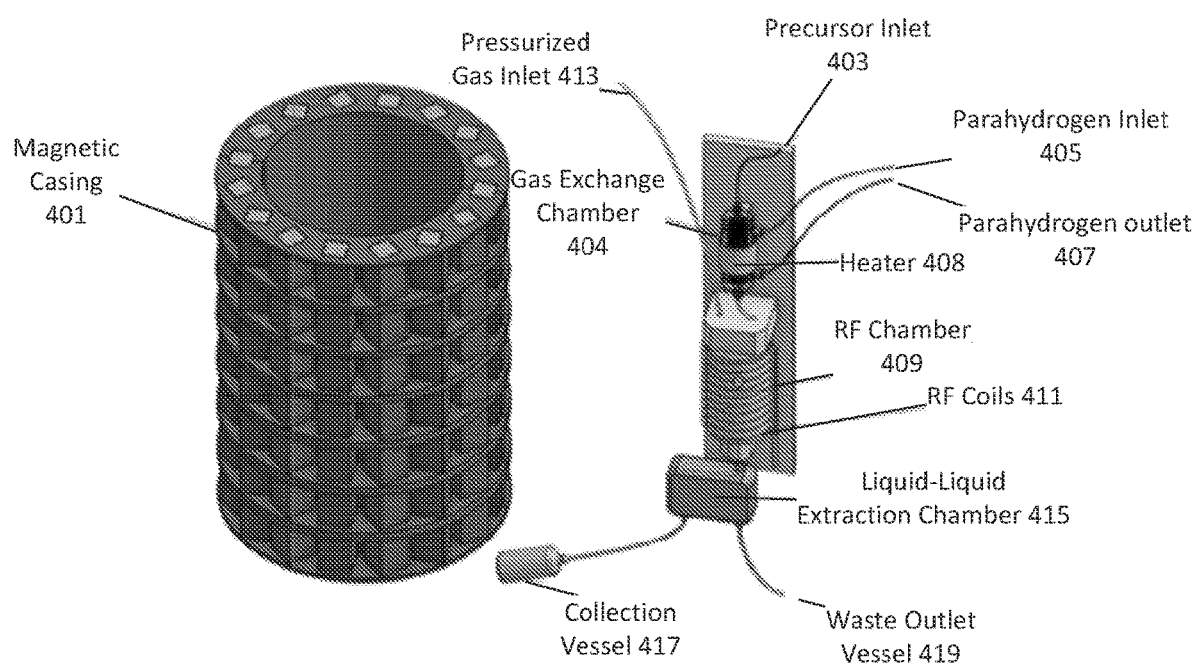
FIG. 4 illustrates an exemplary large-scale PHIP polarizer with greater than 1 ml volumes and inhomogeneous magnetic field, consistent with disclosed embodiments.

Design of a Large-Scale PHIP Polarizer with High Volume and Inhomogeneous Magnetic Field FIG. 4 illustrates an exemplary embodiment of a design of a PHIP polarizer. While described with regards to a PHIP polarizer, the disclosed magnetic field configuration and RF stimulation protocol can be used more generally to polarize NMR materials.

A Halbach magnet array may include a magnet casing 401 with an inner diameter of 5 mm, and may produce fields of 0.3 T. Magnetic casing 401 surrounds chambers for hydrogenation and RF coils (shown separately from the magnetic casing in FIG. 4). An organic solvent containing precursor molecules and homogeneous catalysts may be conveyed through an inlet 403 to a gas exchange chamber 404. Parahydrogen gas may be conveyed into the same chamber through a parahydrogen inlet 405, where it is brought into contact with the precursor molecules in the solution and produces a hydrogenation reaction (thereby generating parahydrogenated precursor molecules). Excess parahydrogen can exit chamber 404 through parahydrogen outlet 407. A temperature of the parahydrogenated precursor molecules in the gas exchange chamber 404 can be controlled by heater 408. The parahydrogenated precursor molecules may be conveyed to the RF chamber 409 for excitation by RF pulses. Between 1 and 60 ml of the solution (e.g., approximately 1 ml, 5 ml, 10 ml, 30 ml, or 60 ml) may be subject to RF excitation. RF coils 411 for producing the RF pulses may be connected to an arbitrary waveform generator and amplifier. In some embodiments, the arbitrary waveform generator and amplifier may be capable of producing $B_1=2.5$ Gauss excitation in the chamber. In some embodiments, a mean magnetic field strength within the chamber can be between 1 mT and 6000 mT and a magnetic field inhomogeneity within the chamber can be no less than 10 ppm and no more than 1000 ppm. In some embodiments, the magnetic field inhomogeneity in the chamber can approximately 200 ppm. In some embodiments, the mean magnetic field can be between 100 and 500 mT or between 100 and 5000 mT. In some embodiments, the magnetic field inhomogeneity can be between 1 and 250 microtesla (µT), or between 7 µT and 25 µT, or between 7 µT and 50 µT. In some embodiments, the Halbach magnet array can be a nonsuperconducting magnet array and the mean magnetic field strength can be between 100 and 2500 mT. Following polarization transfer by the sequence of RF pulses (thereby generating polarized precursor molecules), the solvent can be mixed with an aqueous solution. In some embodiments, the aqueous solution may optionally contain sodium hydroxide for cleavage of a sidearm of the polarized precursor molecules (thereby generating polarized target molecules). In some embodiments, after mixing, the aqueous solution may be quickly ejected from the chamber for RF excitation by pressurized gas, which may be conveyed through gas inlet 413. The mixed solvents may be pushed into liquid-liquid extraction chamber 415, where the organic phase with the catalysts may be conveyed to the waste outlet 419 while the polarized target molecules in the aqueous phase may be collected in the collection vessel 417.

Pulse Sequences for Polarization Transfer at High Inhomogeneous Fields

Various embodiments of the present disclosure disclose a method for improving the polarization transfer. In some embodiments, the method may promote polarization transfer even in the presence of a large proton FWHM, resulting for example from a large magnetic field inhomogeneity. In some embodiments, the method can include providing a waveform including tens to hundreds of pulses. These pulses can be provided to protect against the detrimental effects of magnetic field inhomogeneity on polarization transfer.

In some preferred embodiments, a pulse sequence for polarization may be configured to transfer the spin order from non-equivalent two $^1$H hydrogenated spins (e.g., when the chemical shift difference is larger than the J coupling between them, which is typically smaller than 15 Hz). In many molecules the chemical shift between the hydrogenated protons is larger than 0.5 ppm, and are considered non-equivalent in a large magnetic field range within the targeted magnetic fields of 100 mT-5000 mT, for example for many molecular esters where the hydrogenation occurs on the side arms. ESOTHERIC, for example, may be a pulse sequence suited for polarization transfer in this regime.

In some alternate embodiments, the pulse sequence may be configured to transfer the spin order from equivalent $^1$H hydrogen spins, e.g., when the chemical shift difference is smaller than the J coupling between them. An example of such a sequence may be Goldman's sequence or S2hM. Both pulse sequences can use the differential J coupling of the $^{13}$C spin to the $^1$H spins to break the singlet order and transfer magnetization to the $^{13}$C spin by multiple $\pi$ and $\pi/2$ pulses. This may be the case for symmetric molecules or for many precursor molecules which are molecular esters where the hydrogenation occurs on the side arm in magnetic fields of earth magnetic field, up to 100 mT.

A degree of magnetic field inhomogeneity may be necessary for achieving high polarization and engineering robustness. However, this inhomogeneity can introduce time-dependent noise due to the diffusive motion of the molecules. As shown below in FIG. 5, attempting to compensate for this effect using currently known pulse techniques may not be feasible due to cumulative pulses errors, which may be caused by the large proton linewidth in the inhomogeneous field. Various embodiments of the present disclosure introduce robust dynamical decoupling which enables multiple pulses without destroying the nuclear coherence due to accumulated pulse errors, (detuning/B1 variations or fluctuations) and for efficient decoupling from the noise due to diffusion in the inhomogeneous magnetic field.

Figure 5:
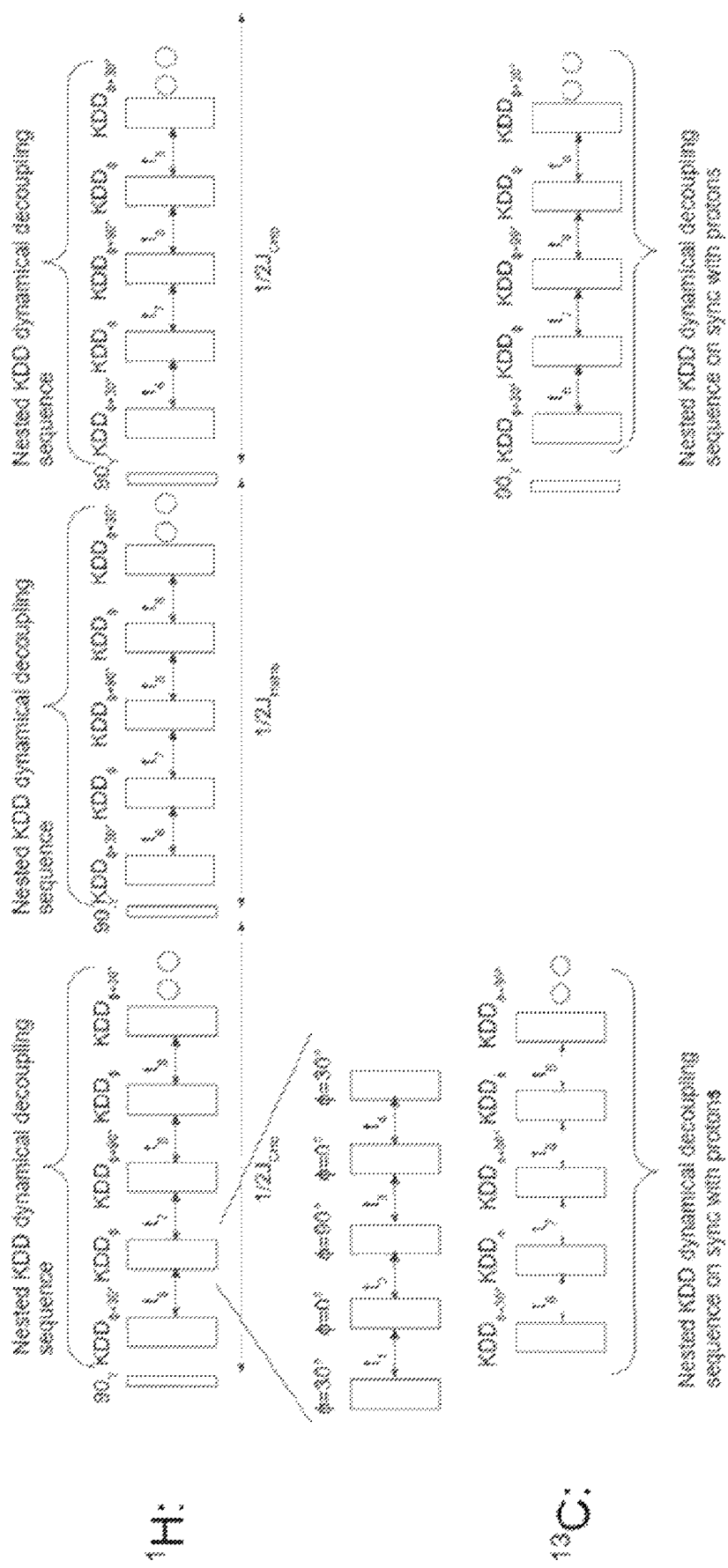
FIG. 5 illustrates an exemplary novel pulse sequence for protecting coherence and enabling high efficiency of polarization transfer in inhomogeneous fields, consistent with disclosed embodiments.

FIG. 5 depicts an RF waveform for protecting coherence and enabling high efficiency of polarization transfer in inhomogeneous fields, using the framework of the ESOTHERIC pulse sequence. The RF waveform can include decoupling sequences. The decoupling sequences can include a series of refocusing pulses which may protect the important evolution times from time-varying dynamics due to the molecular diffusion. Moreover, by correctly choosing the phases of the pulses, pulse errors due to the large inhomogeneous broadening of a sample, as well as B1 errors and fluctuations, may be corrected even for hundreds or thousands of refocusing pulses.

In some embodiments, at least two RF waveforms can be applied to a sample to transfer polarization from parahydrogen to nuclear spins of molecules in the sample. In some embodiments, the at least two RF waveforms may differ. A $^1$H waveform can be a combination of excitation, inversion or other type of pulses, including periods of long RF irradiation. The $^1$H waveform can include a sequence of at least six elements: three excitation pulses, each followed by a decoupling sequence. A decoupling sequence can include multiple pulse blocks. A $^{13}$C waveform can be a combination of excitation, inversion or other type of pulses, including periods of long RF irradiation. The $^{13}$C waveform can include a sequence of at least three elements: an excitation pulse preceded and followed by a decoupling sequence. The decoupling sequence can include multiple pulse blocks. In some embodiments, the $^{13}$C waveform can further include an excitation pulse preceding the first pulse block.

In some embodiments, a pulse sequence can be provided according to a template. The template can specify a pulse sequence for performing nuclear spin polarization. In the non-limiting example depicted in FIG. 5, the template includes a framework for the polarization transfer, such as ESOTHERIC, and sequences of pulses or pulse blocks for dynamical decoupling. A pulse block is a sequence of pulses with durations between them. For example, the pulse block in FIG. 5 includes 5 pulses. Each of the pulses can be a pi pulse. In some embodiments, a time between each pulse in the pulse block (e.g., times t1, t2, t3, and t4 depicted in FIG. 5) may be substantially the same. In some embodiments, at least some of the times between pulses in the pulse block may differ. The values of the times (or mean value of the times) between each pulse in the pulse block can be selected to produce an echo at the time of the next pulse of the polarization transfer framework. In some embodiments, the values of the times (or mean value of the times) between each pulse in the pulse block may be less than a proton Hahn-echo relaxation time (e.g., a T2 relaxation time). In some embodiments, each of the pi-pulses in the pulse block may cause a 180 degree nuclear spin rotation around an axis disposed in a plane (e.g., the x-y plane). The axis of rotation may form an angle (phi) with a reference axis in the x-y plane. Phi may differ between pulses. In some embodiments, phi may range from 0 to 180 degrees. In some embodiments, pulses in a pulse block may alternate between non-zero and zero values of phi. For example, in some embodiments and as depicted in FIG. 5, when the pulse block includes five pulses, phi for the 5 pulses may be 30 degrees, 0 degrees, 90 degrees, 0 degrees and 90 degrees, in that order.

In the sequence of pulses or pulse blocks, each of the pulse blocks or pulses can be based on a template, such as the template described above. The axis of rotation for each pulse in a pulse block can depend on a position of the pulse block in the sequence of pulse blocks. For example, an offset value can be added to the value of phi for each pulse in the pulse block, or each pulse with a non-zero value for phi in the pulse block. The offset may differ between pulses. In some embodiments, the offset may range from 0 to 90 degrees. In some embodiments, offsets may alternate between non-zero and zero values for successive pulse blocks in the sequence. For example, in some embodiments and as depicted in FIG. 5, when the sequence of pulse blocks includes five pulse blocks, the first pulse block has an offset of 30 degree, and second pulse block has an offset of 0 degree, the third pulse block has an offset of 90 degrees, the forth pulse block has an offset of 0 degrees, and the fifth pulse block has an offset of 30 degrees. The RF waveform may include multiple iterations of such a sequence of pulse blocks. The disclosed pattern of offset values may repeat for pulse blocks in subsequent iterations. For example, the first pulse block of the second iteration may have an offset of 30 degrees, while the second pulse block of the third iteration may have an offset of 0 degrees.

In some embodiments, the pulse block sequence may be a KDD-4, KDD-8, KDD-16, KDD-N, XY-4, XY-8, or XY-16 pulse sequence (or a modified version thereof); or a similar sequence of pulses selected to protect nuclear coherence from accumulated pulse errors (e.g., pulse errors arising from detuning, or B1 variations or fluctuations) and for efficient decoupling from the noise due to diffusion in the inhomogeneous magnetic field. Inter-pulse timing and axis of rotation angles can depend, according to known relationships, on the type of pulse sequences. The dynamical decoupling pulse sequence can be repeated as many times as desired. In some embodiments, the total number of pulses in each pulse block sequence may be more than 10, more than 50, or more than 100. In other embodiments, the pulses in the pulse block can cause effects other than 180 degree rotations, including rotations by an angle different than 180 degrees, inversions or other point to point pulses, as long as the pulse block is configured to preserve the coherence of the nuclear spin states and produce an echo at the time of the next pulse of the polarization transfer framework. Consistent with disclosed embodiments, a decoupling sequence can be used within an existing polarization transfer framework, such as PH-INEPT, PH-INEPT+, ESOTHERIC and Goldman's sequence.

Figure 6:
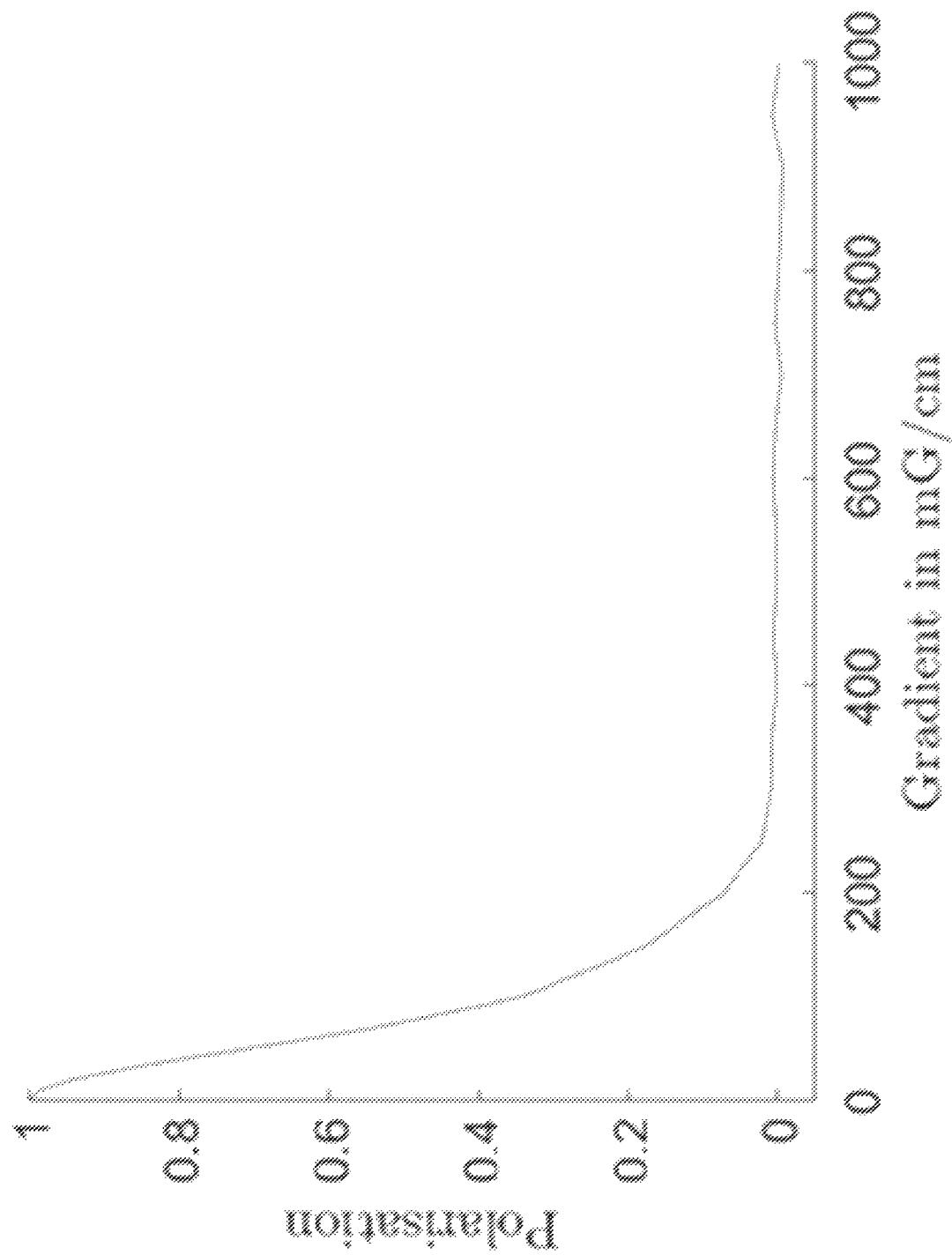
FIG. 6 illustrates exemplary simulated polarization efficiencies of ESOTHERIC for varying magnetic field gradients, in accordance with disclosed embodiments.

Diffusion of particles in an inhomogeneous magnetic field may negatively affect polarization transfer efficiency. FIG. 6 depicts exemplary simulated polarization efficiencies of ESOTHERIC for varying magnetic field gradients. Polarization efficiency can be the percentage of the spin order of the parahydrogenated protons that is transferred to the $^{13}C$ nuclear spin. In this simulation, the stimulation pulses are instantaneous and without amplitude or timing errors. As shown in FIG. 6, ESOTHERIC performance can decrease as magnetic field gradients increase, corresponding to increasing field inhomogeneity (e.g., in a 0.5T magnetic field, 100 ppm over 1 cm diameter would correspond to 500-1000 mG/cm gradient, depending on the field profile).

Figure 7:
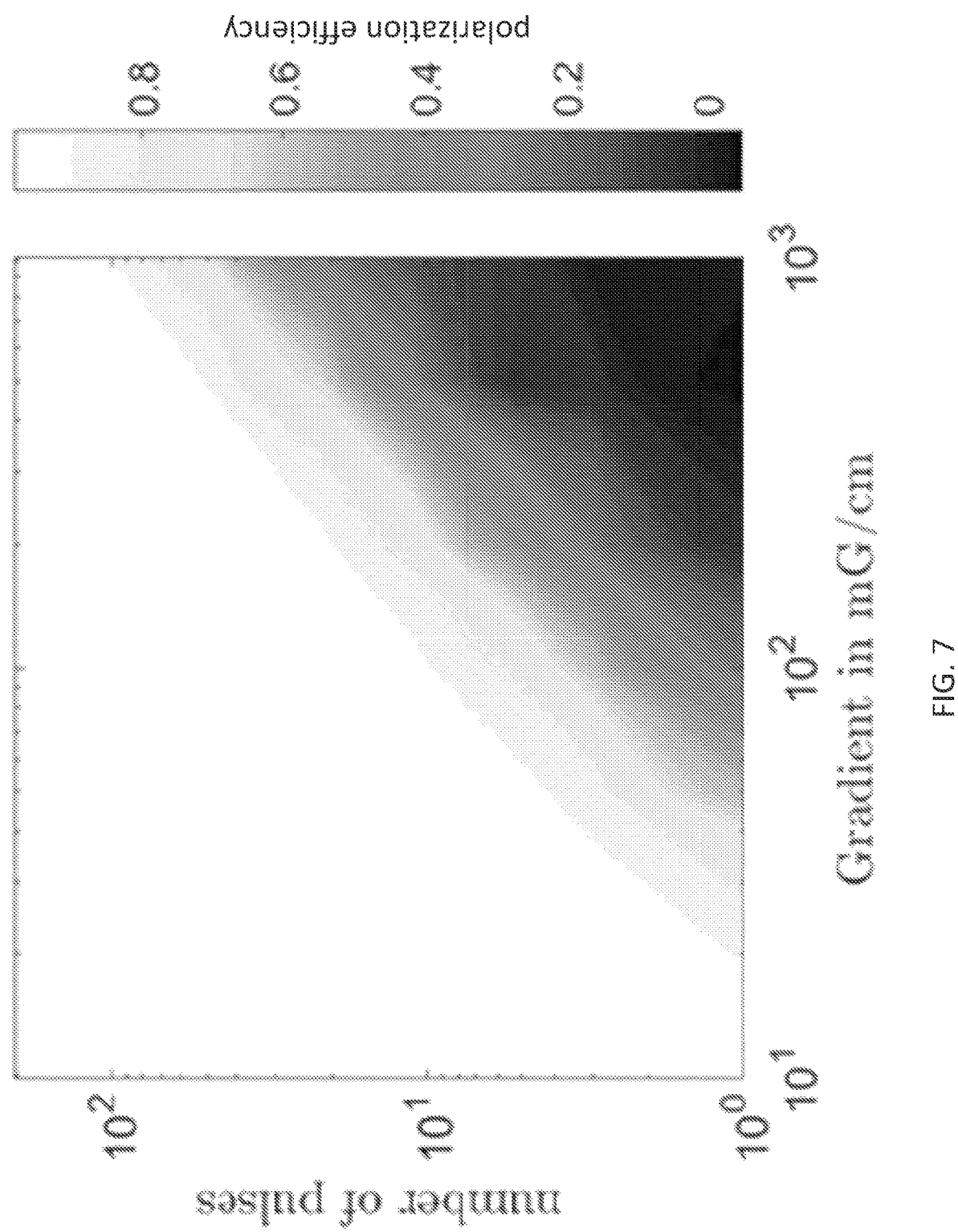
FIG. 7 illustrates exemplary simulated polarization efficiencies for ESOTHERIC with varying magnetic field gradients and varying numbers of refocusing pulses, in accordance with disclosed embodiments.

Consistent with disclosed embodiments, increasing the number of refocusing pulses can reduce the effect of diffusion in the inhomogeneous field on the coherence time, thereby improving polarization transfer efficiency in inhomogeneous fields. FIG. 7 depicts exemplary simulated polarization efficiencies for ESOTHERIC with varying magnetic field gradients and varying numbers of refocusing pulses. The number of refocusing pulses can be the number of pulses in each of the three blocks of the sequence. As shown in FIG. 7, polarization transfer efficiency can increase with the number of refocusing pulses in each block and decrease with increasing magnetic field inhomogeneity. Consistent with disclosed embodiments, polarization transfer efficiencies in excess of 80% may ideally be obtained by using a suitable number of pulses, even in the presence of substantial inhomogeneities (e.g., 50 pulses or more can be used to achieve more than 80% polarization transfer efficiency in a field exhibiting 100 ppm inhomogeneities).

Figure 8:
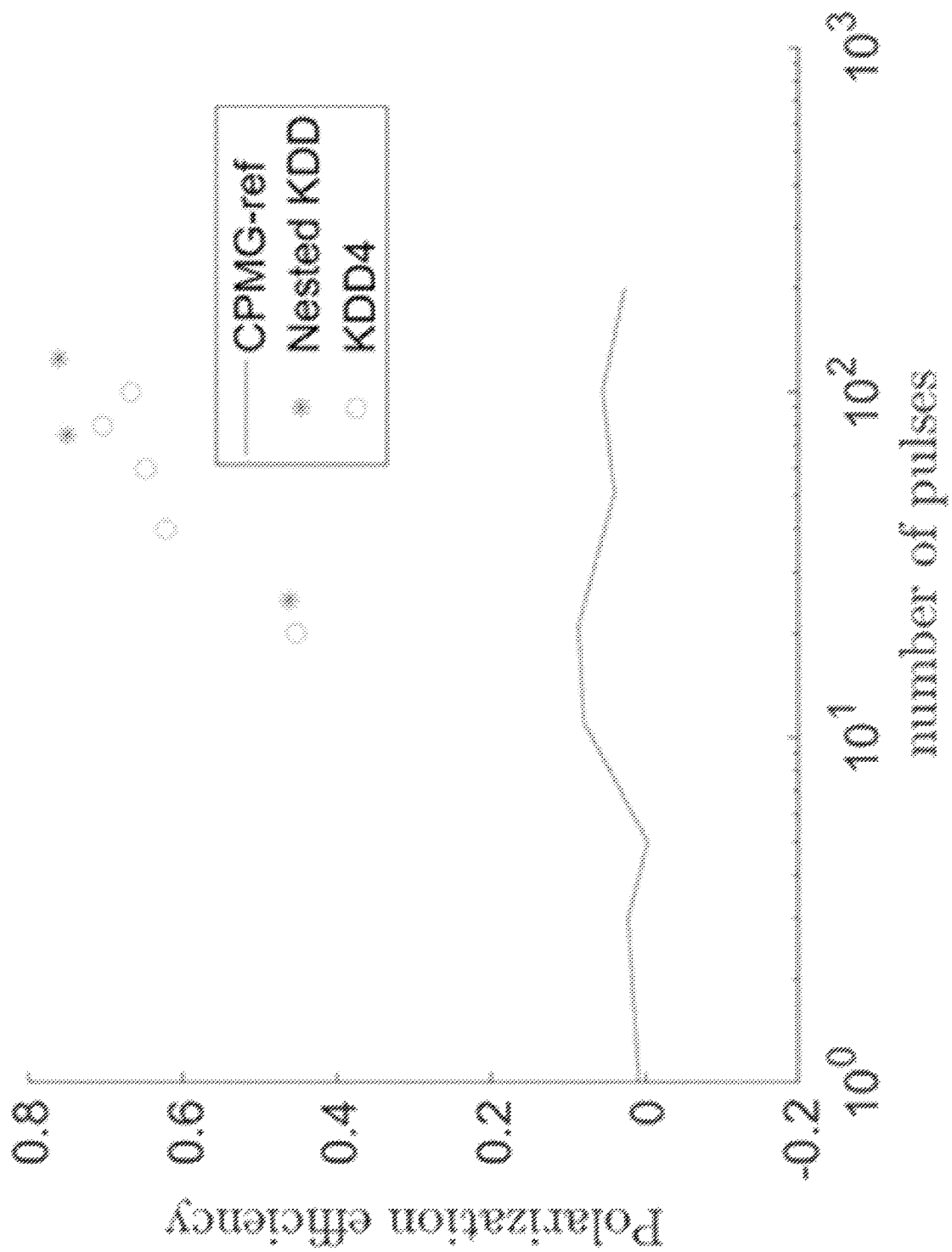
FIG. 8 depicts the effect of nuclear spin linewidth errors on polarization transfer efficiency for several exemplary stimulation sequences, in accordance with disclosed embodiments.

However, increasing the number of pulses may introduce additional errors. In particular, in inhomogeneous fields the errors due to the large linewidth of the sample nuclear spins may prevent efficient transfer of polarization. FIG. 8 depicts the effect of such errors on polarization transfer efficiency for several exemplary stimulation sequences (ESOTHERIC with conventional CPMG decoupling composite pulses (ESOTHERIC-ref, also termed CPMG-ref), Nested KDD, and KDD-4 refocusing pulses). In this non-limiting example, polarization transfer efficiency was assessed in a 0.5T magnetic field, 2.5 G B1 field, with 200 ppm inhomogeneity and parabolic field profile. As shown in FIG. 8, high polarization efficiency may not be achieved when there are high field inhomogeneities (even with relatively strong Rabi frequency of 10 kHz on the $^1H$ spins or when adding refocusing pulses to ESOTHERIC or using ESOTHERIC-ref). However, using sophisticated pulse sequences such as KDD-4 and tailored pulses, the sequences remain sufficiently robust to enable polarization transfer at 100 ppm inhomogeneity.

In some preferred embodiments, the number of pulses in each block may be more than 10, more than 50, or more than 100. This may be performed with dynamic decoupling sequences which are robust to detuning and pulse errors. An example sequence may be the family of KDD-N pulses (e.g. KDD-4, KDD-8, KDD-16) sequences. In these types of DD sequences, the spacing between the refocusing pulses can vary, though as typically for dynamical decoupling sequences, the echo should coincide with the timing of the 90 pulses of the ESOTHERIC sequence. In sequence blocks where the proton and carbons spins are meant to be coupled, the DD sequence may be applied on both $^1H$ and $^{13}C$ spins. In sequence blocks where the $^1H$ and $^{13}C$ spins are decoupled, in some embodiments, DD sequences may be applied on both the $^1H$ and $^{13}C$ spins so that the spins remain decoupled. For example, a symmetric KDD sequence may be applied on the $^1H$ spins and an asymmetric KDD sequence on the carbon spins. In other embodiments, DD sequences may be applied only on the $^1H$ spins in these blocks.

In some preferred embodiments, shaped pulses instead of rectangular pulses may be used for enhanced robustness of the pulses to frequency detuning. In preferred embodiments, the shapes, phases and amplitudes of the pulses are optimized using optimal control. This can be done with a variety of optimization algorithms, including GRAPE and CRAB type of optimization. In certain embodiments, a part of the sequence or even the entire sequence can be optimized, and not only individual pulses. This may be preferred as the molecules only have a few $^1H$, $^2H$, $^{13}C$ or $^{15}N$ nuclear spins with the couplings between the spins well characterized. Examples of pulse sequence optimization is using cooperative pulses.

Pulse Sequence for Polarization Transfer in the Equivalence Regime

In some preferred embodiments, a pulse sequence for polarization may be configured to transfer the spin order from equivalent two $^1H$ hydrogenated spins, e.g., when the chemical shift difference is smaller than the J coupling between them. This is the case in some embodiments in the magnetic fields of 0.01 mT-1500 mT, for example for many molecular esters where the hydrogenation occurs on the side arms. For some symmetric molecules, e.g. fumarate, succinate, where there is no or very small chemical shift between the hydrogenated proton spins, this regime holds for magnetic fields above 1500 mT as well. PulsePol, for example, may be a pulse sequence suited for polarization transfer in this regime.

Figure 9A:
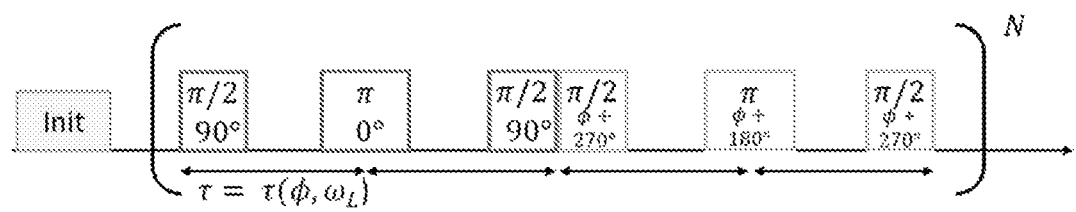
FIG. 9A depicts an exemplary generalized PulsePol sequence, in accordance with disclosed embodiments.
Figure 9B:
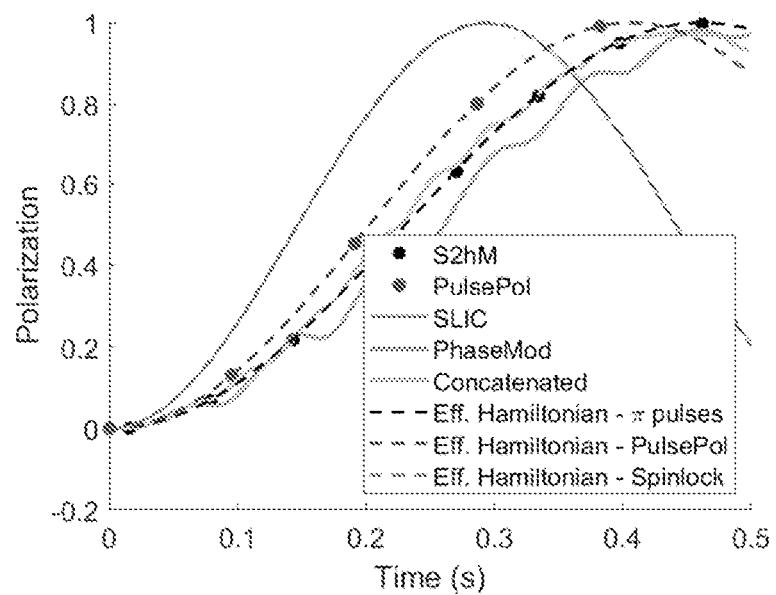
FIG. 9B depicts exemplary rates of polarization transfer using the PulsePol sequence as compared to the S2hM and SLIC sequences, as well as PhaseMod and concatenated drive, in accordance with disclosed embodiments.
Figure 9C:
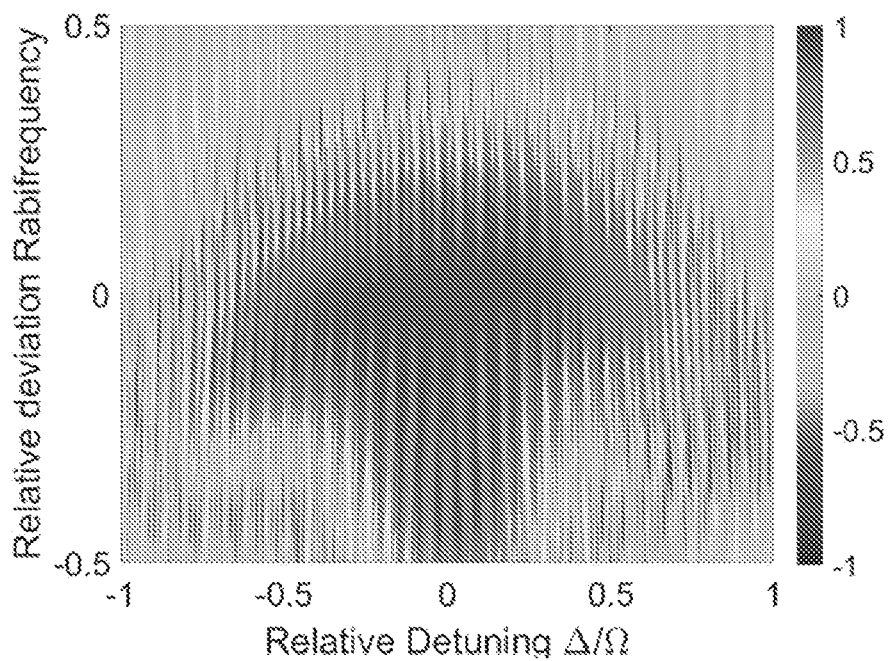
FIGS. 9C and 9D depict the robustness to errors of the polarization transfer for optimized S2hM (composite pulses and alternating phases) and PulsePol, in accordance with disclosed embodiments.
Figure 9D:
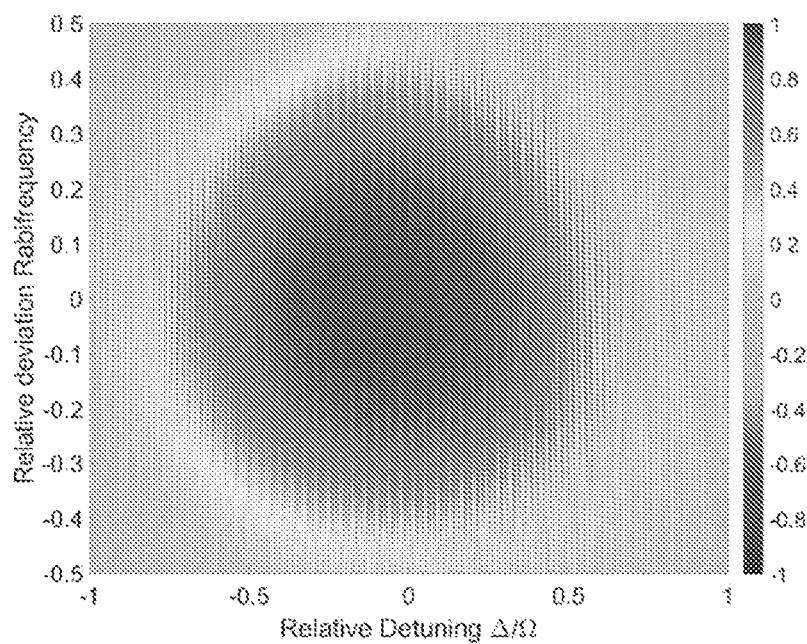

Unlike existing sequences in this regime such as S2hM, it is advantageous that the pulse sequence is designed such that a flip-flop Hamiltonian, producing polarization dynamics, is produced in a time scale which is shorter than the full duration of the sequence. Preferably the flip-flop Hamiltonian dynamics are produces at durations shorter than $1/(J_{13}-J_{23})$, with $(J_{13}-J_{23})$ describes the difference in J-coupling (in units of Hz) between the carbon spin and the individual hydrogenated $^1H$ spins, preferably shorter than $\frac{1}{2}(J_{13}-J_{23})$, $\frac{1}{4}(J_{13}-J_{23})$, $\frac{1}{8}(J_{13}-J_{23})$. The PulsePol sequence, derived initially for dynamic nuclear polarization of nuclear spins by electron spins, is an example of such a sequence. The PulsePol sequence achieves an effective Hamiltonian that allows for polarization exchange between a driven spin and an undriven system by matching the waiting time between pulses to certain multiples of the governing frequency of the undriven system. We have shown analytically and numerically that the form of the sequence that was developed for polarization transfer from nitrogen vacancy (NV) centers in diamond can be directly applied to PHIP systems. FIG. 9A depicts an exemplary generalized PulsePol sequence, in accordance with disclosed embodiments. Choosing $$\phi = \frac{\pi}{2}$$

gives the standard PulsePol sequence. Here the carbon nuclear spin takes the role of the driven spin, the hydrogen spins in a singlet state are the undriven system with an energy gap defined by the J-coupling, which takes a similar role than the nuclear Larmor frequency in the case of the NV system. The coupling between those systems is given by the difference in J-coupling, in contrast to the dipole-dipole interaction in the case of the NV system. Denoting the carbon spin operators by $S_i=\sigma_i/2$, where $\sigma_i$ are the corresponding Pauli matrices, and the spin operators between the inner triplet state $|T_0\rangle$ and the singlet state $|S_0\rangle$ by $I_x=|S_0\rangle\langle T_0|/2+$h. c., $I_y=|S_0\rangle\langle T_0|/2+$h. c. and $I_z=|T_0\rangle\langle T_0|/2-|S_0\rangle\langle S_0|/2$, an effective polarization transfer interaction $H=(2+\sqrt{2})/3\pi\times 2\pi\times(J_{13}-J_{23})\times(S_xI_x\pm S_yI_y)$ is achieved when the pulse spacing fulfills $\tau=3\pi/(4\times 2\pi\times J_{12})$. Here $J_{12}$ is the J-coupling between the hydrogen spins and $(J_{13}-J_{23})$ describes the difference in J-coupling between the carbon spin and the individual hydrogen spins. Different resonance conditions $$\tau = \left(n + \frac{1}{2} \pm \frac{\phi}{2\pi}\right) \times \frac{\pi}{2\pi J_{12}}$$

can be used for an integer n, with the same implication as for the NV center system. In addition, by changing the value of φ the resonance condition can be tuned to almost any value. In numerical simulations we show that the PulsePol sequence offers a drastically improved robustness to control errors compared to SLIC methods, and comparable robustness to control errors with faster transfer rates compared to S2hM. The effective interaction is created at a timescale of few pulses, which is advantageous over S2hM methods that only achieve transfer when fully applied. FIG. 9B depicts exemplary rates of polarization transfer using the PulsePol sequence as compared to the S2hM and SLIC sequences, as well as PhaseMod and concatenated drive, in accordance with disclosed embodiments. Compared to S2hM, PulsePol transfers the magnetization faster. FIG. 9C depicts the depicts the robustness of polarization transfer for S2hM with composite pulses and alternating phases of the form "++−−", while FIG. 9D depicts the robustness of polarization transfer for the PulsePol sequence with optimized φ (φ=π−1.19). It can be seen that even with the composite pulses and phase variations of S2hM, PulsePol is still more robust, demonstrating the efficiency of the transfer.

In some embodiments in the targeted magnetic fields of 0.05 mT-500 mT or for symmetric molecules at fields of 0.05 mT or higher, a continuous wave sequence is used for the polarization transfer. However, the existing sequences such as SLIC are not sufficiently robust to microwave amplitude deviations and magnetic field inhomogeneity, and other sweep-based approaches are significantly slower in the transfer of the spin order. Accordingly, continuous wave sequence can be used or PHIP polarization transfer. This continuous wave sequence can provide additional robustness to the sequence using RF irradiation with at least one additional frequency or using an oscillatory phase modulation of the driving RF field. Disclosed embodiments include polarization transfer methods using concatenated driving or phase-modulated driving.

Figure 10A:
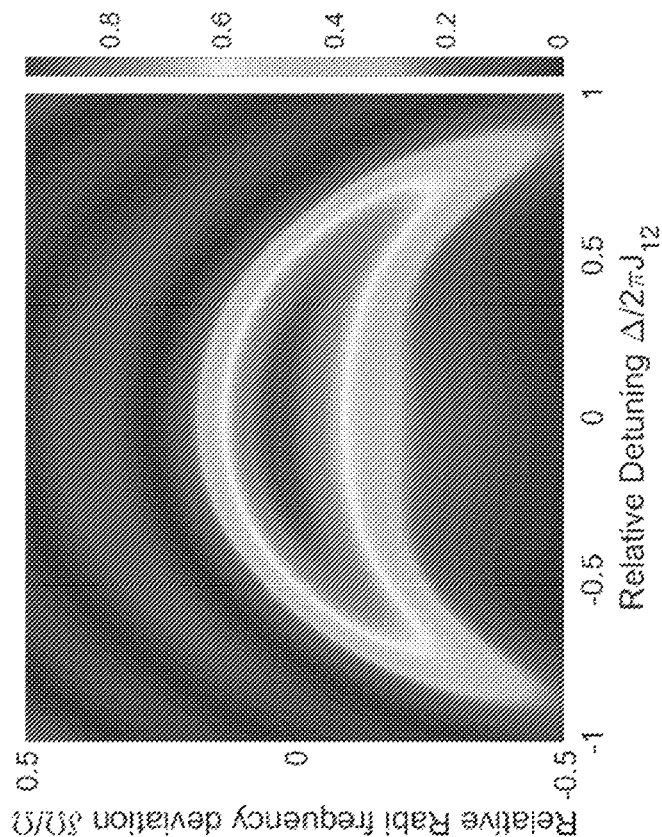
FIGS. 10A and 10B compare robustness to errors between SLIC and concatenated driving, in accordance with disclosed embodiments.
Figure 10B:
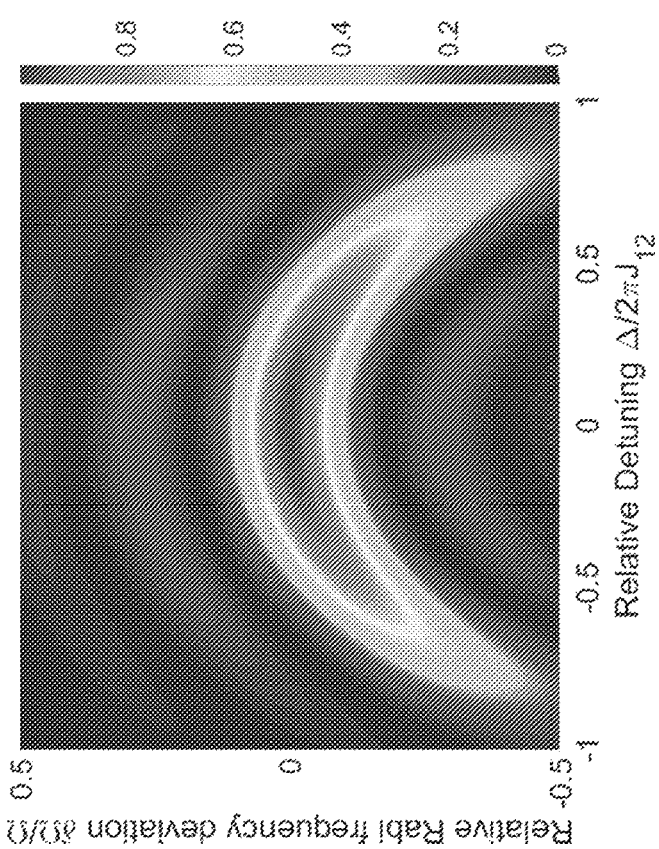

Similarly to the PulsePol sequence, phase modulated and concatenated driving schemes have been originally developed for dynamic nuclear polarization applications, but can be directly transferred to PHIP systems. Their basic principle is similar to NOVEL or SLIC protocols, however the polarization transfer Hamiltonian is achieved in a second rotating frame of reference, which is well decoupled from the usual frame of reference where the dynamics are prone to fluctuations in the radiofrequency amplitude and magnetic field inhomogeneities. The basic driving that is applied to the carbon nuclear spin is described by a Hamiltonian $H_d=\Omega_1|e\rangle\langle g|/2\ e^{2i\ sin(\Omega_1 t)\Omega_2/\Omega_1}+$h. c. for the phase-modulated scheme and $H_d=\Omega_1S_x+2\Omega_2S_y\cos(\Omega_1 t)$ for the concatenated driving, where we neglect the description of driving errors for simplicity. Note that for the PHIP applications the ratio $(J_{13}-J_{23})/J_{12}$ between the coupling to the carbon spin and the hydrogen J-coupling is typically larger than for the electron spin systems it was developed for, so additional frequency shifts that can be found numerically may be incorporated. Phase modulated and concatenated driving schemes can improve robustness to control errors compared to SLIC while maintaining or even reducing energy input into the system. FIGS. 10A and 10B compare robustness to errors between SLIC (FIG. 10A) and concatenated driving (FIG. 10B).

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

The embodiments may further be described using the following clauses:

1. A system for increasing nuclear spin polarization, comprising: a chamber configurable to contain at least 1 milliliter (mL) of a solution comprising a precursor at a concentration of between 10 and 1000 millimolar (mM); a radiofrequency (RF) coil disposed around the chamber, the RF coil comprising a proton (1H) channel and a carbon-13 (13C) channel; a magnetic field source configured to generate a magnetic field, the magnetic field having, withing the chamber, a mean magnetic field strength between 1 and 6000 millitesla (mT) and a magnetic field inhomogeneity between 1 and 250 microtesla (µT); a flow manifold coupled to a gas-liquid exchange mechanism configurable to mix parahydrogen gas with the solution to generate a parahydrogenated precursor; and a waveform generator configurable to generate a polarized precursor by providing RF stimulation to the RF coil, a nuclear spin polarization of the polarized precursor at least 10%, the RF stimulation comprising: (i) a first pulse sequence, provided to the 1H channel, comprising at least one 1H excitation pulse and a first set of at least ten 1H dynamic decoupling pulses; and (ii) a second pulse sequence, provided to the 13C channel, comprising at least one 13C excitation pulse, and a second set of at least ten 13C dynamic decoupling pulses.

2. The system of clause 1, wherein the concentration of the precursor is between 10 and 100 mM.

3. The system of any one of clauses 1 and 2, wherein the mean magnetic field strength generated within the chamber is between 100 and 5000 mT.

4. The system of any one of clauses 1 and 2, wherein the mean magnetic field strength generated within the chamber is between 100 and 500 mT.

5. The system of any one of clauses 1-4, wherein the magnetic field source is a nonsuperconducting magnet and the mean magnetic field strength generated within the chamber is between 100 and 2500 mT.

6. The system of any one of clauses 1-5, wherein the first pulse sequence comprises a mean time between each 1H dynamic decoupling pulses of the first set is less than a 1H spin-echo coherence time of the compound.

7. The system of any one of clauses 1-6, wherein the gas-liquid exchange mechanism comprises a bubbler.

8. The system of any one of clauses 1-7, wherein the gas-liquid is configurable to mix the parahydrogen gas with the solution by a diffusion mechanism.

9. The system of any one of clauses 1-8, wherein the gas-liquid exchange mechanism comprises a membrane configured to permit diffusion of the parahydrogen into the solution.

10. The system of any one of clauses 1-9, further comprising an extraction mechanism configurable to reduce a concentration of a hydrogenation catalyst in the solution to less than 100 nanomolar (nM).

11. The system of clause 10, wherein: the extraction mechanism is configurable to perform a liquid-liquid separation of the hydrogenation catalyst into a first liquid and a polarized target molecule cleaved from the polarized precursor into a second liquid.

12. The system of any one of clauses 10-11, wherein: the extraction mechanism is configurable to reduce the concentration of the hydrogenation catalyst based on a difference in binding affinity between the hydrogenation catalyst and a polarized target molecule cleaved from the polarized precursor.

13. The system of any one of clauses 10-12, wherein the extraction mechanism is configurable to mechanically separate the hydrogenation catalyst from a polarized target molecule cleaved from the polarized precursor.

14. The system of any one of clauses 10-13, wherein following the liquid-liquid separation, a concentration of a polarized target molecule cleaved from the polarized precursor in the second liquid is at least 100 millimolar (mM).

15. The system of any one of clauses 1-14, wherein a median time between each pulse of the first set is less than an inverse of a 1H J-coupling constant of the precursor.

16. The system of any one of clauses 1-15, wherein the first pulse sequence comprises at least two pulses with different phases and a time interval of at least 10 microseconds (µs) between the at least two pulses.

17. The system of any one of clauses 1-16, wherein each pulse in the first set comprises a non-rectangular shape.

18. The system of any one of clauses 1-17, wherein the magnetic field source comprises a permanent magnet.

19. The system of any one of clauses 1-18, wherein a 1H full width half maximum (FWHM) linewidth following the at least one 1H excitation pulse is at least 40 Hertz (Hz).

20. The system of any one of clauses 1-19, wherein the magnetic field source comprises a Halbach magnet array.

21. The system of any one of clauses 1-20, wherein the precursor includes a target molecule bound to a sidearm.

22. The system of any one of clauses 1-21, wherein the precursor comprises an ester of pyruvate.

23. The system of any one of clauses 1-22, wherein the magnetic field inhomogeneity within the chamber is between 7 µT and 50 µT.

24. The system of any one of clauses 1-22, wherein the magnetic field inhomogeneity within the chamber is between 7 µT and 25 µT.

25. The system of any one of clauses 1-24, wherein the nuclear spin polarization of the polarized precursor comprises a nuclear spin polarization of at least one 13C atom in the polarized precursor.

26. A method for increasing a nuclear spin polarization, comprising: generating a parahydrogenated precursor by flowing a parahydrogen gas into a chamber containing at least 1 milliliter (mL) of a solution comprising a precursor at a concentration of between 10 and 1000 millimolar (mM), the chamber disposed within a magnetic field, the magnetic field having a mean magnetic field strength of between 1 and 5000 millitesla (mT) and a magnetic field inhomogeneity of between 1 and 250 microtesla (µT) within the chamber; mixing the parahydrogen gas with the solution; and generating a polarized precursor by applying a first pulse sequence and a second pulse sequence to increase the nuclear spin polarization of the parahydrogenated precursor to at least 10%, wherein: the first pulse sequence comprises at least one proton (1H) excitation pulse and a first set of a least ten 1H dynamic decoupling pulses; and the second pulse sequence comprises at least one carbon-13 (13C) excitation pulse, and a first set of a least ten 13C dynamic decoupling pulses.

27. The method of clause 26, wherein the concentration of the precursor is between 10 and 100 mM.

28. The method of clauses 26-27, wherein the mean magnetic field strength generated within the chamber is between 100 and 5000 mT.

29. The method of any one of clauses 26-27, wherein the mean magnetic field strength generated within the chamber is between 100 and 500 mT.

30. The method of any one of clauses 26-29, wherein the magnetic field source is a nonsuperconducting magnet and the mean magnetic field strength generated within the chamber is between 100 and 2500 mT.

31. The method of any one of clauses 26-30, wherein a mean time between each 1H dynamic coupling pulse of the first set is less than a 1H relaxation time of the precursor.

32. The method of any one of clauses 26-31, wherein the mixing the parahydrogen gas with the solution comprises bubbling the parahydrogen gas into the solution.

33. The method of any one of clauses 26-32, wherein the mixing the parahydrogen gas with the solution comprises mixing the parahydrogen gas with the solution using a diffusion mechanism.

34. The method of any one of clauses 26-33, wherein the mixing the parahydrogen gas with the solution comprises mixing the parahydrogen gas with the solution using a membrane.

35. The method of any one of clauses 26-34, further comprising reducing a concentration of a hydrogenation catalyst in the solution to less than 100 nanomolar (nM).

36. The method of clause 35, wherein: reducing the concentration of the hydrogenation catalyst comprises performing a liquid-liquid separation of the hydrogenation catalyst into a first liquid and a polarized target molecule cleaved from the polarized precursor into a second liquid.

37. The method of any one of clauses 35-36, wherein: reducing the concentration of the hydrogenation catalyst comprises reducing the concentration of the hydrogenation catalyst based on a difference in binding affinity between the hydrogenation catalyst and a polarized target molecule cleaved from the polarized precursor.

38. The method of any one of clauses 35-37, wherein the reducing the concentration of the hydrogenation catalyst comprises mechanically separating the hydrogenation catalyst from a polarized target molecule cleaved from the polarized precursor.

39. The method of any one of clauses 35-38, wherein, following the liquid-liquid separation, a concentration of a polarized target molecule cleaved from the polarized precursor in the second liquid is at least 100 millimolar (mM).

40. The method of any one of clauses 26-39, wherein a median time between each pulse of the first set is less than an inverse of a $^1$H J-coupling constant of the polarized target molecule.

41. The method of any one of clauses 26-40, wherein the first pulse sequence comprises at least two pulses with different phases and a time interval of at least 10 microseconds (µs) between the at least two pulses.

42. The method of any one of clauses 26-41, wherein each pulse in the first set comprises a non-rectangular shape.

43. The method of any one of clauses 26-42, wherein the magnetic field is provided by a permanent magnet.

44. The method of any one of clauses 26-43, wherein a $^1$H full width half maximum (FWHM) linewidth following the at least one $^1$H excitation pulse is at least 40 Hertz (Hz).

45. The method of any one of clauses 26-44, wherein the magnetic field is provided by a Halbach magnet array.

46. The method of any one of clauses 26-45, wherein the precursor includes a target molecule bound to a sidearm.

47. The method of any one of clauses 26-46, wherein the precursor comprises an ester of pyruvate.

48. The method of any one of clauses 26-47, wherein the magnetic field inhomogeneity within the chamber is at least 7 µT.

49. The method of any one of clauses 26-47, wherein the magnetic field inhomogeneity within the chamber is between 7 µT and 50 µT.

50. The method of any one of clauses 26-47, wherein the magnetic field inhomogeneity within the chamber is between 7 µT and 25 µT.

51. The method of any one of clauses 26-50, wherein the nuclear spin polarization of the polarized precursor comprises a nuclear spin polarization of at least one $^{13}$C atom in the polarized precursor.

52. A method for preparing a polarized target molecule for use in a magnetic resonance operation, comprising: generating and storing parahydrogen at a first location; transporting the parahydrogen from the first location to a second location different from the first location; at the second location, generating a solution of a parahydrogenated precursor by mixing the parahydrogen with a solution of a precursor in the presence of a hydrogenation catalyst; generating, using the solution of the parahydrogenated precursor, a solution of a polarized precursor by transferring polarization from protons associated with the parahydrogen in the parahydrogenated precursor to at least one nuclear spin of the parahydrogenated precursor, thereby obtain a polarization in the solution of the polarized precursor of at least 10% in the at least one nuclear spin; generating, using the solution of the polarized precursor, a solution of a polarized target molecule by cleaving the polarized target molecule from the polarized precursor; generating, using the solution of a polarized target molecule, a second solution of the polarized target molecule by separating the hydrogenation catalyst from the second solution of the polarized target molecule, the second solution of the polarized target molecule having a concentration of at least 100 mM of the target molecule.

53. The method of clause 52, wherein the precursor comprises an ester of the target molecule.

54. The method of any one of clauses 52-53, wherein the precursor comprises the target molecule bound to a sidearm.

55. The method of any one of clauses 52-54, wherein cleaving the polarized target molecule from the polarized precursor comprises cleaving the polarized target molecule from a sidearm.

56. The method of any one of clauses 52-55, wherein the precursor comprises an ester of pyruvate.
57. The method of any one of clauses 52-56, wherein the method further comprises performing an NMR or MRI scan using the target molecule.
58. The method of any one of clauses 52-57, wherein transferring the polarization from the protons associated with the parahydrogen to the at least one nuclear spin of the molecule comprises:
  a. providing, to the solution of the parahydrogenated precursor, a first pulse sequence comprising a first set of at least ten $^1$H dynamic decoupling pulses;
  b. applying, to the solution of the parahydrogenated precursor, a magnetic field comprising a mean magnetic field strength of between 1 and 5000 millitesla (mT) and a magnetic field inhomogeneity of between 1 and 250 microtesla (µT) with the solution;
  c. applying, to the solution of the parahydrogenated precursor, a second pulse sequence comprising at least three $^1$H excitation pulses; and
  d. applying, to the solution of the parahydrogenated precursor, a third pulse sequence comprising a second set of at least ten $^{13}$C dynamic decoupling pulses.
59. The method of any one of clauses 54-58, wherein separating the hydrogenation catalyst from the second solution of the polarized target molecule comprises:
  a. extracting the polarized target molecule into the second solution of the polarized target molecule through a liquid-liquid extraction process.
60. The method of clause 59, wherein the liquid-liquid extraction process comprises extracting the hydrogenation catalyst into an organic phase or a fluorinated phase and extracting the target molecule into an aqueous phase.
61. A compound of Formula I,

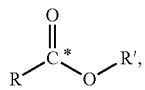

(I)

tautomers, deuterated derivatives and their tautomers, or pharmaceutically acceptable salts, thereof, and $^{13}$C enriched derivatives of any of the foregoing, wherein C* denotes $^{13}$C; R is a linear, branched, or cyclic $C_1$-$C_{10}$ alkyl group, in which one or more C atoms maybe be replaced by CO, COOH, CH$_2$COOH, CONH$_2$, and R is optionally substituted with, one or more group(s) selected from a CO, an OH, an amino (NR$^1$R$^2$), a halogen atom(s), a halo-alkyl group(s), or a carbocycle, wherein the carbocycle is optionally substituted with an aliphatic or aromatic ring, which is optionally substituted by one or more functional groups. R' is a linear, branched or cyclic hydrocarbon $C_1$-$C_{10}$ alkyl group containing an unsaturated bond in a two-bond distance from C*, in which one or more C atoms maybe be replaced by CO, COOH, CH$_2$COOH, CONH$_2$, and R' is optionally substituted with, one or more functional group(s), selected from a halogen, a halo-alkyl group, and a carbocycle, wherein the carbocycle is optionally substituted with an aliphatic or aromatic ring, which is optionally substituted by one or more functional groups; R$^1$ and R$^2$ are each independently H, $^2$H, $^3$H or an amino protecting group, optionally selected from trifluoroacetyl, acetyl, benzoyl, carbobenzoxy, tert-butyl carbonate and benzyl, 62. A compound of clause 61, wherein R is $C_1$-$C_3$ alkyl in which one or more C atoms maybe be replaced by a carbonyl, CO.
63. A compound of any one of clauses 61-62, wherein R is $C_1$-$C_3$ alkyl in which one or more C atoms may be replaced by CO, COOH, CH$_2$COOH, CONH$_2$, and R is optionally substituted with, one or more group(s) selected from a carbonyl (C=O), a hydroxyl (—OH), an amino (NR$^1$R$^2$), a halogen, a halo-alkyl, or a carbocycle, wherein the carbocycle is optionally substituted with an aliphatic or aromatic ring, wherein the aliphatic or aromatic ring is optionally substituted with one or more functional groups, and R$^1$ and R$^2$ are each independently selected from H, $^2$H, $^3$H and an amino protecting group, optionally selected from trifluoroacetyl, acetyl, benzoyl, carbobenzoxy, tert-butyl carbonate and benzyl,
64. A compound of clause 61, wherein R is acetyl (CH$_3$CO)
65. A compound of Formula II,

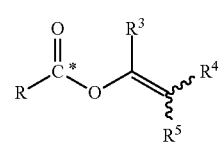

(II)

wherein, R is a linear, branched, or cyclic $C_1$-$C_{10}$ alkyl group, in which one or more C atoms maybe be replaced by CO, COOH, CH$_2$COOH, CONH$_2$, and R is optionally substituted with, one or more group(s) selected from carbonyl (C=O), hydroxyl (—OH), amino (NR$^1$R$^2$), halogen atom(s), halo-alkyl group(s), or by a carbocycle optionally substituted with an aliphatic or aromatic ring, which is, in its turn, optionally substituted by one or more functional groups; R$^1$ and R$^2$ are each independently selected from H, $^2$H, $^3$H and an amino protecting group, optionally selected from trifluoroacetyl, acetyl, benzoyl, carbobenzoxy, tert-butyl carbonate and benzyl; R$^3$, R$^4$, and R$^5$ are each independently H or a linear, branched, or cyclic $C_1$-$C_{10}$ alkyl hydrocarbon, wherein no more than two of the three of R$^3$, R$^4$, and R$^5$ may be a proton or deuterated species, thereof, wherein the hydrocarbon is optionally substituted with one or more group(s) selected from a $C_6$ aryl, benzyl, phenyl, heteroaryl, halogen, a haloalkyl, an optionally substituted carbocycle, and an optionally substituted heterocycle, which is, each in its turn, optionally substituted by one or more functional groups selected from alkyl, alkoxy, or a heteroatom, such as N, O, Si, P, S, or a halogen such as F, Cl, Br, I that may also be further substituted
66. A compound of clause 65 wherein only one of R$^3$, R$^4$, and R$^5$ is hydrogen, or a deuterated species thereof.
67. A compound of clause 65 wherein only two of R$^3$, R$^4$, and R$^5$ is hydrogen, or a deuterated species thereof.
68. A compound of clause 65 wherein R$^3$ and R$^4$ are independently selected from H, D, a $C_1$-$C_{10}$ cycloalkyl, a $C_1$-$C_6$ aryl, and a heteroaryl.

69. A compound of any one of clauses 65-68 wherein, the $^1$H atoms on the unsaturated carbons of the ester are optionally and independently replaced by $^2$H or $^3$H atoms.
70. A compound of Formula IIa,

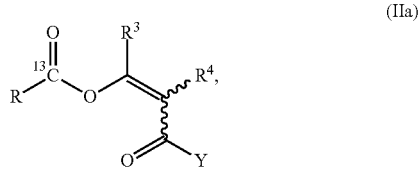

(IIa)

wherein R is a linear, branched, or cyclic $C_1$-$C_{10}$ alkyl group, in which one or more C atoms maybe be replaced by CO, COOH, $CH_2COOH$, $CONH_2$, and R may be optionally substituted with, one or more group(s) selected from carbonyl (C=O), hydroxyl (—OH), amino ($NR^1R^2$), halogen atom(s), haloalkyl group(s), or by a carbocycle optionally substituted with an aliphatic or aromatic ring, which is, in its turn, optionally substituted by one or more functional groups; $R^1$ and $R^2$ are each independently selected from H, $^2$H, $^3$H and an amino protecting group, optionally selected from F, trifluoroacetyl, acetyl, benzoyl, carbobenzoxy, tert-butyl carbonate and benzyl; $R^3$ and $R^4$ are each independently H or a linear, branched, or cyclic $C_1$-$C_{10}$ alkyl hydrocarbon, wherein the hydrocarbon is optionally substituted with one or more group(s) selected from a $C^6$ aryl, benzyl, phenyl, heteroaryl, halogen, a haloalkyl, an optionally substituted carbocycle, and an optionally substituted heterocycle, which is, each in its turn, optionally substituted by one or more functional groups selected from alkyl, alkoxy, or a heteroatom, such as N, O, Si, P, S, or a halogen such as F, Cl, Br, I that may also be further substituted; Y is selected from $R^x$, $OR^x$, $SR^x$, $NR^x_2$, or H, wherein $R^x$ is alkyl, cycloalkyl ($C_1$-$C_{18}$), aryl ($C_1$-$C_6$), heteroaryl, or H wherein one or more C atoms may be optionally substituted with alkyl ($C_1$-$C_6$), or aryl ($C_1$-$C_6$).
71. A compound of clause 70 wherein R is acetyl ($CH_3CO$)
72. A compound of any one of clauses 70-71 wherein $R^x$ is acetyl ($CH_3CO$).
73. A compound of any one of clauses 70-71 wherein $R^x$ is benzyl.
74. A compound of Formula IIb,

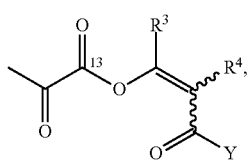

(IIb)

wherein $R^3$ and $R^4$ are each are each independently H or a linear, branched, or cyclic $C_1$-$C_{10}$ alkyl hydrocarbon, wherein the hydrocarbon is optionally substituted with one or more group(s) selected from a $C^6$ aryl, benzyl, phenyl, heteroaryl, halogen, a haloalkyl, an optionally substituted carbocycle, and an optionally substituted heterocycle, which is, each in its turn, optionally substituted by one or more functional groups selected from alkyl, alkoxy, or a heteroatom, such as N, O, Si, P, S, or a halogen such as F, Cl, Br, I) that may also be further substituted; Y is $R^x$, $OR^x$, $SR^x$, $NR^x2$, or H, wherein $R^x$ is selected from alkyl ($C_1$-$C_{10}$), aryl ($C_1$-$C_6$), heteroaryl, or H wherein one or more C atoms may be optionally substituted with alkyl ($C_1$-$C_6$), or aryl aryl ($C_1$-$C_6$).
75. The compound of clause 74, wherein, only one of $R^3$ and $R^4$ is hydrogen, or a deuterated species thereof.
76. The compound of clause 74, wherein, only two of $R^3$ and $R^4$ is hydrogen is hydrogen, or a deuterated species thereof.
77. The compound of clause 74 wherein $R^3$ and $R^4$ are independently selected from H, D, a $C_1$-$C_{10}$ cycloalkyl, a $C_1$-$C_6$ aryl, and a heteroaryl.
78. The compound of any one of clauses 74-77 wherein $R^x$ is benzyl.
79. A compound of any one of clauses 74-77 wherein Y is $CH_3$.
80. A compound of clause 74 wherein $R^3$ and $R^4$ are independently selected from H, $^2$H, and $^3$H, Y is $CH_3$.
81. A compound of Formula IIc,

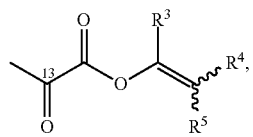

(IIc)

wherein $R_3$, $R_4$, and $R_5$ are each independently H or a linear, branched, or cyclic $C_1$-$C_{10}$ alkyl hydrocarbon, wherein the hydrocarbon is optionally substituted with one or more group(s) selected from a $C^6$ aryl, benzyl, phenyl, heteroaryl, halogen, a haloalkyl, an optionally substituted carbocycle, and an optionally substituted heterocycle, which is, each in its turn, optionally substituted by one or more functional groups selected from alkyl, alkoxy, or a heteroatom, such as N, O, Si, P, S, or a halogen such as F, Cl, Br, or I that may also be further substituted;
82. A compound of clause 81 wherein $R^3$ and $R^4$ are independently selected from H, $^2$H, cycloalkyl ($C_1$-$C_{10}$), aryl ($C_6$-$C_{10}$), and heteroaryl and $R^5$ is a carbonyl optionally substituted with H, D, cycloalkyl ($C_1$-$C_{10}$), or aryl ($C_6$-$C_{10}$).
83. A compound of any one of clauses 81-82 wherein $R^3$ and $R^4$ are independently selected from H, $^2$H, and $^3$H
84. A compound of any one of clauses 81-83, wherein $R^5$ is phenyl
85. A compound of clause 81 wherein $R^3$ and $R^4$ are independently selected from H, $^2$H, and $^3$H, and $R_5$ is phenyl
86. A compound of clause 81 wherein $R^3$ and $R^4$ are H, or a deuterated version, thereof, and $R^5$ is phenyl
87. A compound according to Formula (III):

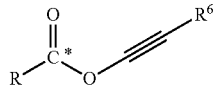

(III)

wherein, R is a linear, branched, or cyclic $C_1$-$C_{10}$ alkyl group, in which one or more C atoms maybe be replaced by CO, COOH, $CH_2COOH$, $CONH_2$, and R may be optionally substituted with, one or more group(s) selected from carbonyl (C=O), hydroxyl (—OH), amino ($NR^1R^2$), halogen atom(s), halo-alkyl group(s), or by a carbocycle optionally substituted with an aliphatic or aromatic ring, which is, in its turn, optionally substituted by one or more functional groups; $R^1$ and $R^2$ are each independently selected from H, $^2H$, $^3H$ and an amino protecting group, optionally selected from trifluoroacetyl, acetyl, benzoyl, carbobenzoxy, tert-butyl carbonate and benzyl; $R^6$ is H, or a linear, branched, or cyclic $C_1$-$C_{10}$ alkyl hydrocarbon, wherein the hydrocarbon is optionally substituted with one or more group(s) selected from a $C_6$-$C_{10}$ aryl, benzyl, phenyl, heteroaryl, halogen, a haloalkyl, an optionally substituted carbocycle, and an optionally substituted heterocycle aryl or cycloalkyl groups, which is, each in its turn, optionally substituted by one or more functional groups selected from alkyl, alkoxy, or a heteroatom, such as N, O, Si, P, S, or a halogen, such as F, Cl, Br, I that may also be further substituted.

Other embodiments will be apparent from consideration of the specification and practice of the embodiments disclosed herein. It is intended that the specification and examples be considered as an example only, with a true scope and spirit of the disclosed embodiments being indicated by the following claims.

What is claimed is:

1. A system for increasing nuclear spin polarization, comprising:
    a chamber configurable to contain at least 1 milliliter (mL) of a solution comprising a precursor at a concentration of between 10 and 1000 millimolar (mM);
    a radiofrequency (RF) coil disposed around the chamber, the RF coil comprising a proton (1H) channel and a carbon-13 ($^{13}C$) channel;
    a magnetic field source configured to generate a magnetic field, the magnetic field having, within the chamber, a mean magnetic field strength between 1 and 6000 millitesla (mT) and a magnetic field inhomogeneity between 1 and 250 microtesla (µT);
    a flow manifold coupled to a gas-liquid exchange mechanism configurable to mix parahydrogen gas with the solution to generate a parahydrogenated precursor; and
    a waveform generator configurable to generate a polarized precursor by providing RF stimulation to the RF coil, a nuclear spin polarization of the polarized precursor at least 10%, the RF stimulation comprising:
        (i) a first pulse sequence, provided to the 1H channel, comprising at least one 1H excitation pulse and a first set of at least ten 1H dynamic decoupling pulses; and
        (ii) a second pulse sequence, provided to the 13C channel, comprising at least one 13C excitation pulse, and a second set of at least ten 13C dynamic decoupling pulses.

2. The system of claim 1, wherein the concentration of the precursor is between 10 and 100 mM.

3. The system of claim 1, wherein the mean magnetic field strength generated within the chamber is between 100 and 5000 mT.

4. The system of claim 1, wherein the mean magnetic field strength generated within the chamber is between 100 and 500 mT.

5. The system of claim 1, wherein the magnetic field source is a nonsuperconducting magnet and the mean magnetic field strength generated within the chamber is between 100 and 2500 mT.

6. The system of claim 1, wherein the first pulse sequence comprises a mean time between each 1H dynamic decoupling pulses of the first set, the mean time being less than a 1H spin-echo coherence time of the compound.

7. The system of claim 1, wherein the gas-liquid exchange mechanism comprises a bubbler.

8. The system of claim 1, wherein the gas-liquid is configurable to mix the parahydrogen gas with the solution by a diffusion mechanism.

9. The system of claim 1, wherein the gas-liquid exchange mechanism comprises a membrane configurable to permit diffusion of the parahydrogen into the solution.

10. The system of claim 1, further comprising an extraction mechanism configurable to reduce a concentration of a hydrogenation catalyst in the solution to less than 100 nanomolar (nM).

11. The system of claim 10, wherein:
    the extraction mechanism is configurable to perform a liquid-liquid separation of the hydrogenation catalyst into a first liquid and a polarized target molecule cleaved from the polarized precursor into a second liquid.

12. The system of claim 10, wherein: the extraction mechanism is configurable to reduce the concentration of the hydrogenation catalyst based on a difference in binding affinity between the hydrogenation catalyst and a polarized target molecule cleaved from the polarized precursor.

13. The system of claim 10, wherein the extraction mechanism is configurable to mechanically separate the hydrogenation catalyst from a polarized target molecule cleaved from the polarized precursor.

14. The system of claim 10, wherein following the liquid-liquid separation, a concentration of a polarized target molecule cleaved from the polarized precursor in the second liquid is at least 100 millimolar (mM).

15. The system of claim 1, wherein a median time between each pulse of the first set is less than an inverse of a 1H J-coupling constant of the precursor.

16. The system of claim 1, wherein the first pulse sequence comprises at least two pulses with different phases and a time interval of at least 10 microseconds (µs) between the at least two pulses.

17. The system of claim 1, wherein each pulse in the first set comprises a non-rectangular shape.

18. The system of claim 1, wherein the magnetic field source comprises a permanent magnet.

19. The system of claim 1, wherein a 1H full width half maximum (FWHM) linewidth following the at least one 1H excitation pulse is at least 40 Hertz (Hz).

20. The system of claim 1, wherein the magnetic field source comprises a Halbach magnet array.

21. The system of claim 1, wherein the precursor includes a target molecule bound to a sidearm.

22. The system of claim 1, wherein the precursor comprises an ester of pyruvate.

23. The system of claims 1-22, wherein the magnetic field inhomogeneity within the chamber is between 7 µT and 50 µT.

24. The system of claim 1, wherein the magnetic field inhomogeneity within the chamber is between 7 µT and 25 µT.

25. The system of claim 1, wherein the nuclear spin polarization of the polarized precursor comprises a nuclear spin polarization of at least one 13C atom in the polarized precursor.

* * * * *